United States Patent [19]

Gold et al.

[11] Patent Number: 5,348,944

[45] Date of Patent: * Sep. 20, 1994

[54] CARBOXYALKYL DIPEPTIDES

[75] Inventors: Elijah H. Gold; Bernard R. Neustadt, both of West Orange; Elizabeth M. Smith, Verona, all of N.J.

[73] Assignee: Schering Corporation, Kenilworth, N.J.

[*] Notice: The portion of the term of this patent subsequent to May 6, 2003 has been disclaimed.

[21] Appl. No.: 261,815

[22] Filed: Apr. 4, 1988

Related U.S. Application Data

[63] Continuation of Ser. No. 258,484, Apr. 28, 1981, abandoned, which is a continuation-in-part of Ser. No. 201,649, Oct. 28, 1980, abandoned, which is a continuation-in-part of Ser. No. 199,886, Oct. 23, 1980, abandoned.

[51] Int. Cl.$^5$ .................... A61K 37/02; C07K 5/06
[52] U.S. Cl. .................... 514/19; 514/412; 514/414; 548/452
[58] Field of Search .................... 514/19, 412, 414; 548/452

[56] References Cited

U.S. PATENT DOCUMENTS

| | | | |
|---|---|---|---|
| 4,311,697 | 1/1982 | Krapcho | 424/240 |
| 4,316,905 | 2/1982 | Krapcho | 420/274 |
| 4,316,906 | 2/1982 | Ondetti et al. | 424/274 |

Primary Examiner—Lester L. Lee
Attorney, Agent, or Firm—Anita W. Magatti; Eric S. Dicker

[57] ABSTRACT

Compounds of the formula

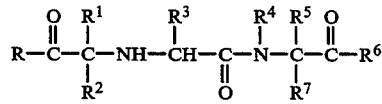

useful as antihypertensive agents are disclosed.

4 Claims, No Drawings

CARBOXYALKYL DIPEPTIDES

This application is a continuation of U.S. Ser. No. 258,484, filed Apr. 28, 1981, and now abandoned, which is a is a continuation-in-part of U.S. Ser. No. 201,649, filed Oct. 28, 1980, now abandoned, which is a continuation-in-part of U.S. Ser. No. 199,886, filed Oct. 23, 1980, now abandoned.

The present invention relates to carboxyalkyl dipeptides which are useful as inhibitors of angiotensin-converting enzyme and as antihypertensive agents.

The compounds of the present invention are compounds of the formula

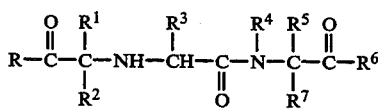

and the pharmaceutically acceptable salts thereof, wherein R and $R^6$ are the same or different and are hydroxy, lower alkoxy, lower alkenoxy, dilower alkylamino lower alkoxy (e.g. dimethylaminoethoxy), acylamino lower alkoxy (e.g. acetylaminoethoxy), acyloxy lower alkoxy (e.g. pivaloyloxyethoxy), aryloxy (e.g. phenoxy), arylloweralkoxy (e.g. benzyloxy), amino, lower alkylamino, dilower alkylamino, hydroxyamino, arylower alkylamino (e.g. benzylamino), or substituted aryloxy or substituted aryllower alkoxy wherein the substituent is methyl, halo or methoxy; $R^1$ is hydrogen, alkyl of from 1 to 10 carbon atoms, including branched and cyclic and unsaturated (e.g. allyl) alkyl groups, substituted lower alkyl wherein the substituent is hydroxy, lower alkoxy, aryloxy (e.g. phenoxy), substituted aryloxy, heteroaryloxy, substituted heteroaryloxy, amino, lower alkylamino, diloweralkylamino, acylmino, arylamino, substituted arylamino, guanidino, imidazolyl, indolyl, lower alkylthio, arylthio (e.g. phenylthio), substituted arylthio, carboxy, carbamoyl, lower alkoxycarbonyl, aryl (e.g. phenyl or naphthyl), substituted aryl, aralkyloxy, substituted aralkyloxy, aralkylthio, or substituted aralkylthio, wherein the aryl or heteroaryl portion of said substituted aryloxy, heteroaryloxy, arylamino, arylthio, aryl, aralkyloxy or aralkylthio groups is substituted with a group selected from halo, loweralkyl, hydroxy, lower alkoxy, amino, aminomethyl, carboxyl, cyano and sulfamoyl; $R^2$ and $R^7$ are the same or different and are hydrogen or lower alkyl; $R^3$ is hydrogen, lower alkyl, phenyl lower alkyl, aminomethylphenyl lower alkyl, hydroxyphenyl lower alkyl, hydroxy lower alkyl, acylamino lower alkyl (e.g. benzoylamino lower alkyl or acetylamino lower alkyl), amino lower alkyl, dimethylamino lower alkyl, guanidino lower alkyl, imidazolyl lower alkyl, indolyl lower alkyl, or lower alkylthio lower alkyl; $R^4$ and $R^5$ are selected from hydrogen, lower alkyl and Z, or $R^4$ and $R^5$ taken together form a group represented by Q, U, V, Y, D or E wherein Z is

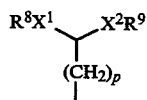

wherein $X^1$ and $X^2$ are independently selected from O, S and $CH_2$, $R^8$ and $R^9$ are independently selected from lower alkyl, lower alkenyl, lower alkynyl, cycloalkyl having 3 to 8 carbon atoms, hydroxy lower alkyl or —$(CH_2)_n Ar$, wherein n is 0, 1, 2, or 3 and Ar is substituted phenyl, furyl, thienyl or pyridyl, wherein said substituted phenyl, furyl, thienyl or pyridyl groups are substituted with at least one group that is independently selected from hydrogen, $C_1$ to $C_4$ alkyl, lower alkoxy, lower alkylthio, halo, $CF_3$ and hydroxy, or $R^8$ and $R^9$ taken together form a bridge W wherein W is a single bond or a methylene bridge or a substituted methylene bridge and one of $X^1$ and $X^2$ is methylene or W is an alkylene or substituted alkylene bridge having 2 or 3 carbon atoms, said substituted methylene bridge or said substituted alkylene bridge having one or two substituents selected from lower alkyl, aryl, and aryl lower alkyl groups, and p is 0, 1 or 2; with the proviso that at least one of $R^4$ and $R^5$ is Z, with the proviso that if $R^4$ is Z and p is 0 then $X^1$ and $X^2$ must both be methylene, and with the proviso that if $X^1$ and $X^2$ are both methylene then $R^8$ and $R^9$ must form an alkylene bridge W; wherein Q is

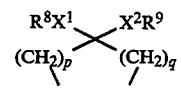

wherein $R^8$, $R^9$, $X^1$ and $X^2$ are as defined above, p is 0, 1 or 2, q is 0, 1 or 2, with the proviso that the sum of p and q must be 1, 2 or 3, with the proviso that if p is 0 then $X^1$ and $X^2$ must be methylene, and with the proviso that if $X^1$ and $X^2$ are methylene then $R^8$ and $R^9$ taken together form a bridge W, wherein W is as defined above; V is

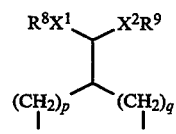

wherein $R^8$ $R^9$ $X^1$ are as defined above, p is 0, 1 or 2 and q is 0, 1 or 2, with the proviso that the sum of p and q is 1, 2 or 3, with the proviso that if $X^1$ and $X^2$ are $CH_2$ then $R^8$ and $R^9$ taken together form a bridge W, wherein W is as defined above, wherein U is

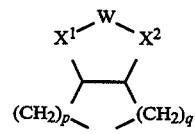

wherein W is as defined above, except that W may be a methylene bridge when $X^1$ and $X^2$ are oxygen or sulfur, $X^1$ and $X^2$ are as defined above, p is 0, 1 or 2, q is 0, or 2, with the proviso that the sum of p and q is 1 or 2, and with the proviso that if p is 0, $X^1$ must be $CH_2$; and wherein Y is

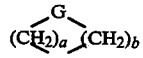

wherein G is oxygen, sulfur or $CH_2$, a is 2, 3 or 4 and b is 1, 2, 3, 4 or 5, with the proviso that the sum of a and b is 5,6 or 7, or G is CH₂, a is 0,1,2 or 3 and b is 0,1,2 or 3 with the proviso that the sum of a and b is 1,2 or 3, with the proviso that the sum of a and b may be 1,2 or 3 only if $R^1$ is lower alkyl substituted with aralkylthio or aralkyloxy (that is, the group Y may be a 2,3 or 4 carbon chain only when $R^1$ is lower alkyl substituted with aralkylthio or aralkyloxy);

wherein D is

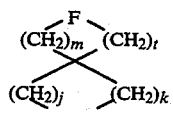

wherein F is O or S, j is 0,1 or 2, k is 0,1 or 2, with the proviso that the sum of j and k must be 1,2 or 3, and m is 1,2 or 3 and t is 1,2 or 3, with the proviso that the sum of m and t must be 2,3 or 4;

and wherein E is

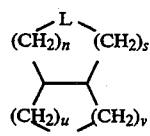

wherein L is O or S, u is 0,1 or 2, v is 0,1 or 2, with the proviso that the sum of u and v must be 1 or 2, and h is 1 or and s is 1 or 2, with the proviso that the sum of h and s must be 2 or 3.

As will be seen from the above descriptions of the compounds of the present invention, when $R^4$ and $R^5$ form a group Q, U, V, Y, D or E, these groups, taken together with the nitrogen to which $R^4$ is attached, and the carbon to which $R^5$ is attached, form various ring systems. Included among these ring systems are the following:

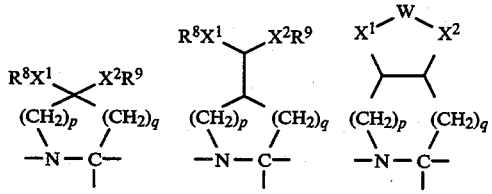

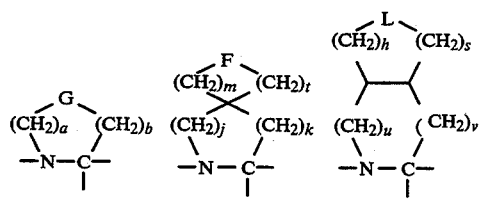

Also, the aforementioned groups $R^8$ and $R^9$ appearing in the groups Z, Q and V, may also form ring systems. Thus, for example when $R^8$ and $R^9$ in the group Z form a bridge W, as described above, the following ring system is formed:

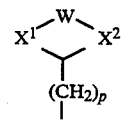

Also, when $R^8$ and $R^9$ in the group Q form a bridge W, as described above, the following ring system is formed:

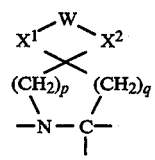

Also, when $R^8$ and $R^9$ in the group V form a bridge W, as described above, the following ring system is formed:

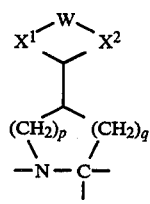

Each of the rings in the structures shown above will have at least four members. The values of p,q,m,t,j,k,h,s,n and v and the chosen definition of W in the rings drawn above will determine whether any of the aforesaid rings will have 5 or 6 or more members.

Thus, one embodiment of the present invention comprises compounds of the formula

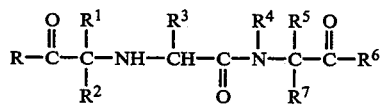

wherein $R^4$ and $R^5$ are selected from hydrogen, lower alkyl and Z, wherein Z, R, $R^1$ $R^2$ $R^3$ $R^6$ and $R^7$ are defined above Another embodiment of the present invention comprises compounds of the formula

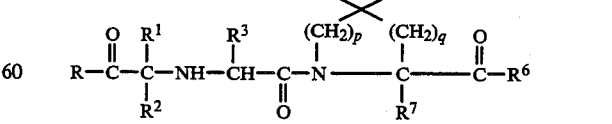

wherein $R^8$, $R^9$, $X^1$, $X^2$, p and q are as defined above for the group Q and wherein R, $R^1$, $R^2$, $R^3$, $R^6$ and $R^7$ are as defined above.

Non-limiting examples of compounds of the formula III are compounds of the formula

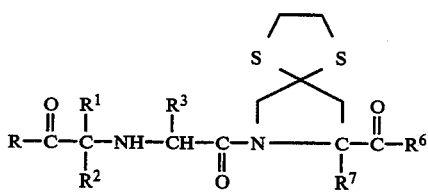

IV wherein R, $R^1$, $R^2$, $R^3$, $R^6$ and $R^7$ are as defined above.

Another embodiment of the present invention comprises compounds of the formula

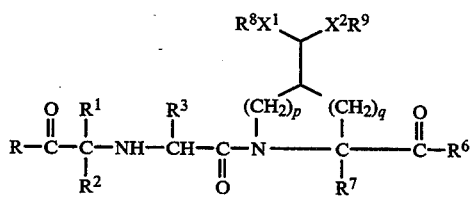

V wherein $R^8$, $R^9$, $X^1$, $X^2$, p and q are as defined above for the group V and wherein R, $R^1$, $R^2$, $R^3$, $R^6$ and $R^7$ are as defined above.

Another embodiment of the present invention comprises compounds of the formula

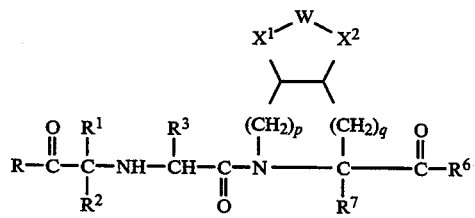

VI wherein $X^1$, $X^2$, W, p and q are as defined above for the group U and R, $R^1$, $R^2$, $R^3$, $R^6$ and $R^7$ are as defined above.

Non-limiting examples of compounds of the formula VI are compounds of the formulae

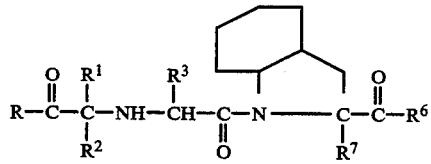

VII and

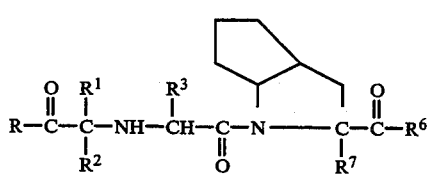

VIII wherein R, $R^1$, $R^2$, $R^3$, $R^6$ and $R^7$ are as defined above
Another embodiment of the present invention comprises compounds of the formula

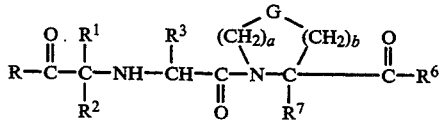

IX wherein G, a and b are as defined above for the group Y and R, $R^1$, $R^2$, $R^3$, $R^6$ and $R^7$ are as defined above Non-limiting examples of compounds of the formula IX are compounds of the formula

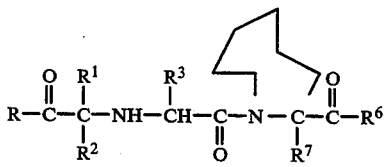

X wherein R, $R^1$, $R_2$, $R^3$, $R^6$ and $R^7$ are as defined above.

Another embodiment of the present invention comprises compounds of the formula

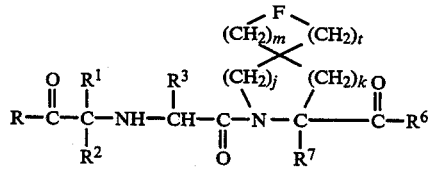

XI wherein F, m, t, j and k are as defined above for the group D and R, $R^1$, $R^2$, $R^3$, $R^6$ and $R^7$ are as defined above.

Another embodiment of the present invention comprises compounds of the formula

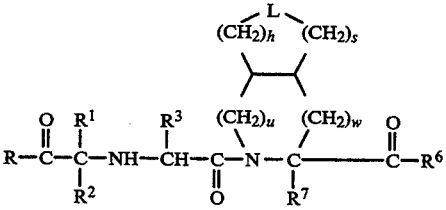

XII wherein L, h, s, u and v are as defined above for the group E and R, $R^1$, $R^2$, $R^3$, $R^6$ and $R^7$ are as defined above.

Preferred subclasses of the present invention are amino acyl-azabicycloalkane carboxylic acids, more preferably alanyl azabicycloalkane carboxylic acids and most preferably N-(alkoxycarbonyl alkylalanyl)-azabicycloalkane carboxylic acids. Aminoacylazabicycloalkane carboxylic acids that are particularly preferred are compounds of the aforementioned formula VII. Alanyl-azabicycloalkane carboxylic acids of the formula VII are more preferred and N-(alkoxycarbonylalkylalanyl)-azabicycloalkane carboxylic acids of the formula VII are most preferred.

Other preferred subclasses of the present invention are N-(alkoxycarbonyl-aralkyloxyalkyl) dipeptides and N-alkoxycarbonyl-aralkylthio-alkyl) dipeptides. Particularly preferred are N-(alkoxycarbonyl-aralkylthioalkyl)-alanyl aminoacids, and most preferred are N-(alkoxycarbonyl-aralkylthioalkyl)-alanyl azacycloalkane carboxylic acids and the corresponding azabicycloalkane carboxylic acids.

The aforementioned compounds of the formula I, as defined above, include all possible stereoisomers. Acyl includes —C—$R_{12}$ wherein $R_{12}$ is lower alkyl, lower alkenyl or aryl. The lower alkyl, lower alkenyl or lower alkyl groups except where noted otherwise are represented by any of the variables including straight and branched chain hydrocarbon radicals from one to six carbon atoms, for example, methyl, ethyl, propyl, isopropyl, butyl, isobutyl, t-butyl, pentyl, isopentyl, hexyl or vinyl, allyl, butenyl and the like. Cycloalkyl groups include bridged and non-bridged groups. The aralkyl groups represented by any of the above variables have from one to four carbon atoms in the alkyl portion thereof and include for example, benzyl, p-methoxybenzyl and the like. Halo means chloro, bromo, iodo or fluoro. Aryl where it appears in any of the radicals except where noted represents phenyl or naphthyl. Heteroaryl groups where they appear include for example pyridyl, thienyl, furyl, indolyl, benzthienyl, imidazolyl and thiazolyl.

The compounds of the present invention can be produced by one or more of the methods and subroutes depicted in the following equations. Reactive groups not involved in the condensations described below such as amino, carboxy, mercapto, etc., may be protected by methods standard in peptide chemistry prior to the coupling reactions and subsequently deprotected to obtain the desired products. Such reactions are demonstrated in the Examples.

Method I, Route 1 ($R^2$=H)

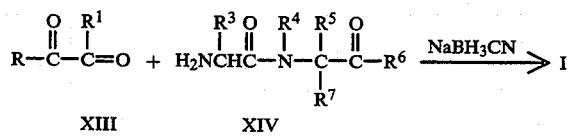

Keto acid (or ester, amide or hydroxamic acid) XIII is condensed with dipeptide XIV in aqueous solution, optimally near neutrality, or in a suitable organic solvent (for example, CH3OH) in the presence of sodium cyanoborohydride to give I ($R^2$=H). Alternatively, the intermediate Schiff base, enamine, or aminol may be catalytically reduced to yield product I, for example, by hydrogen in the presence of 10% palladium on carbon or of Raney nickel. The ratio of diasteriomeric products formed may be altered by choice of catalyst.

If R and $R^6$ are carboxy protecting groups such as alkoxy or benzyloxy or the like, they can be converted by well known methods such as hydrolysis or hydrogenation to I, wherein R and/or $R^6$ are hydroxy. This is also the case in all of the methods referred to below.

Alternatively XIII can be condensed with an amino acid XV.

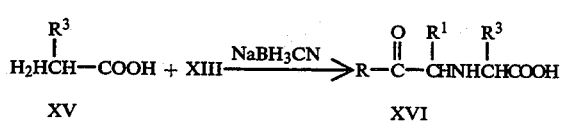

under the same conditions to yield amino acid XVI. Subsequent coupling by known methods with amino acid derivative XVII gives I.

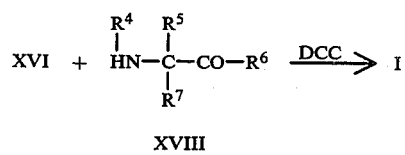

The known methods encompass reactive group protection during the coupling reaction, for example, by N-formyl, N-t-butoxycarbonyl and N-carbobenzyloxy groups followed by their removal to yield I. Furthermore, the R function may include removable ester groups such as benzyl, ethyl, or t-butyl. Condensing agents in this synthetic route are typically those useful in peptide chemistry such as dicyclohexylcarbodiimide (DCC) or diphenylphosphoryl azide (DPPA) or XVI may be activated via the intermediacy of active esters such as that derived from 1-hydroxybenzotriazole.

Route 2

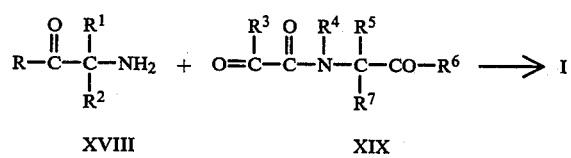

Amino acid (or ester, amide or hydroxamic acid) XVIII is condensed with ketone XIX under conditions described for Route 1 to give I.

Alternatively, the synthesis can be performed in a step-wise fashion by condensing XVIII with keto acid XX to yield amino acid XXI. By known methods, as indicated above

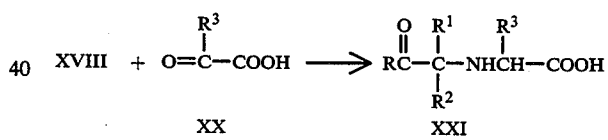

under Route 1, XXI can be condensed with amino acid derivative XVII to give I.

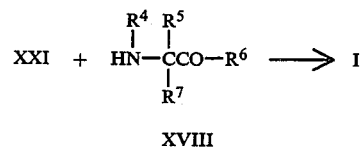

In the special case of $R^1$ bearing an alpha-amino substituent, the carbonyl and amino groups can be conveniently protected as a beta-lactam function.

Method II, Route 1

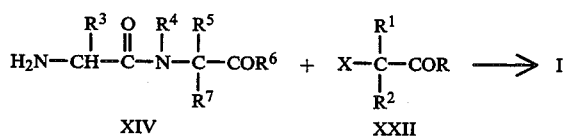

The dipeptide XIV is alkylated with the appropriate alpha-haloacid (ester or amide) or alpha-sulfonyloxy acid (ester or amide) XXII, wherein X is chlorine, bromine, iodine, alkanesulfonyloxy or arenesulfonyloxy, under basic conditions in water or in an organic solvent.

Alternatively, the synthesis can be performed in a step-wise fashion.

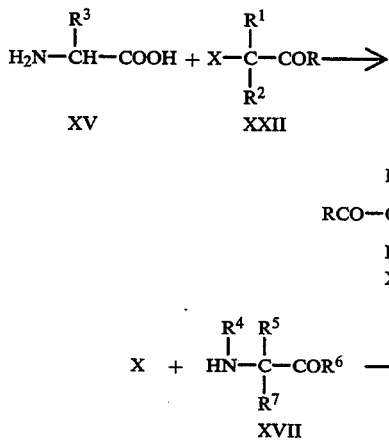

In this stepwise synthesis X in the compound of formula XXII is chlorine, bromine, iodine, alkanesulfonyloxy or arenesulfonyloxy.

The aminoacid XV is alkylated by the alpha-haloacid (ester or amide) or alpha-sulfonyloxy acid (ester or amide) XXII under basic conditions to yield compounds XXI This is condensed by standard methods as indicated under Route 1 with the aminoacid (ester or amide) XVII to afford I.

Reductive cleavage of a benzyl ester I (where $R^6$ is benzyloxy and R is alkoxy) will yield compounds of formula I wherein R is alkoxy and $R^6$ is hydroxy, and where $R^6$ is alkoxy and R is benzyloxy, will yield compounds of formula I wherein R is hydroxy and $R^6$ is alkoxy.

Route 2

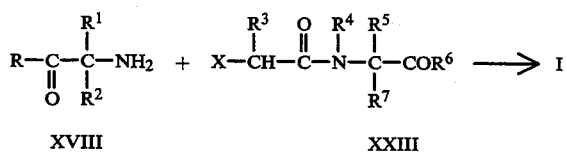

The aminoacid or derivative XVIII is alkylated with the appropriately substituted alpha-haloacetyl or alpha-sulfonyloxy acyl aminoacid XXIII wherein X is chloro, bromo, iodo, alkanesulfonyloxy or arenesulfonyloxy, under basic conditions in water or other solvent to obtain compounds of formula I.

Alternatively, the synthesis can be performed in a step-wise fashion by condensing an aminoacid ester XVIII with a substituted alpha-halocarboxylic acid or a alpha-sulfonyloxy carboxylic acid (XXIV) wherein X is defined as in the paragraph next above, to yield the intermediate XXI. By known methods described under Route 1, XXI can be coupled with an aminoacid XVII or derivative to give I.

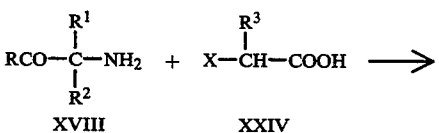

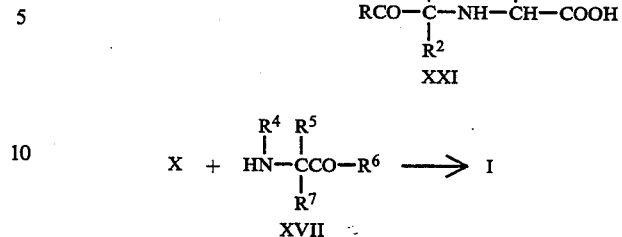

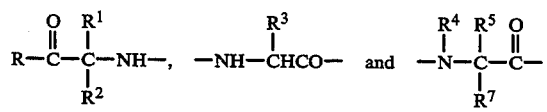

As desired, protecting groups may be removed by known methods.

The starting materials which are required for the above processes herein described are known in the literature or can be made by known methods from known starting materials.

In the compounds of the formula I, the carbon atoms to which $R^1$, $R^3$ and $R^5$ are attached may be asymmetric. The compounds accordingly exist in disastereoisomeric forms or in mixtures thereof. The above described syntheses can utilize racemates, enantiomers or diastereomers as starting materials. Enantiomeric intermediates may be obtained by resolution methods known in the art. When diastereomeric products result from the synthetic procedures, the diastereomeric products can be separated by conventional chromatographic or fractional crystallization methods. In general, the aminoacid part-structures, i.e., $$\begin{array}{ccc} \overset{O}{\underset{\|}{R-C}}-\overset{R^1}{\underset{R^2}{\underset{|}{C}}}-NH-, & -NH-\overset{R^3}{\underset{|}{C}}HCO-\text{ and } & -\overset{R^4}{\underset{|}{N}}-\overset{R^5}{\underset{|}{\underset{R^7}{C}}}-\overset{O}{\underset{\|}{C}}- \end{array}$$

of Formula I are preferred in the configuration most similar to that of natural L-amino acids. Usually, natural L-amino acids are assigned the S-configuration. A notable exception is the natural amino acid L-cysteine which is assigned the R-configuration.

The compounds of this invention form salts with various inorganic and organic acids and bases which are also within the scope of the invention. Such salts include ammonium salts, alkali metal salts like sodium and potassium salts (which are preferred), alkaline earth metal salts like the calcium and magnesium salts, salts with organic bases e.g., dicyclohexylamine salts, N-methyl-D-glucamine, salts with amino acids like arginine, lysine and the like. Also, salts with organic and inorganic acids may be prepared, e.g., HCl, HBr, $H_2SO_4$, $H_3PO_4$, methanesulfonic acid, toluensulfonic acid, maleic acid, fumaric acid and camphorsulfonic acid. The non-toxic physiologically acceptable salts are preferred, although other salts are also useful, e.g., in isolating or purifying the product.

The salts may be formed by conventional means, as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

The following examples illustrate the preparation of the compounds of the present invention. The diasteromers prepared as set forth below may be isolated by column chromatography or by fractional crystallization.

In the Examples below, octahydroindole-2(S)-carboxylic acid refers to cis,syn-octahydroindole-2(S)-carboxylic acid, also named 3a(S),7a(S)-octahydroindole-2(S)-carboxylic acid.

EXAMPLE 1

1-[N-(1-Carbomethoxy-3-phenylpropyl)-(S)-alanyl]octahydroindole-2(S)-carboxylic acid A. Dissolve 27.0 g of ethyl indole-2-carboxylate in 250 ml of trifluoroacetic acid. Add 2.05 g of platinium oxide, hydrogenate the mixture at 50 lb/in$^2$ at room temperature. Filter the mixture and concentrate the filtrate in vacuo to give a residue. Suspend the residue in ether and treat with cold dilute sodium hydroxide solution. Dry the organic layer dried over magnesium sulfate and concentrate it to give ethyl octahydroindole-2-carboxylate, a pale yellow oil. The oil should immediately be used in the following step.

B. To a solution of 10.0 g of ethyl octahydroindole-2-carboxylate (prepared in as shown in paragraph A of this example) in 400 ml of ethyl acetate add 17.0 g of N-benzyloxycarbonyl-(S)-alanine, N-hydroxysuccinimide ester. Stir the reaction mixture at room temperature for 20 hours and concentrate it in vacuo. Place the residue on a column of silica gel (3000 g, 60–200 mesh) and elute with chloroform:ethyl acetate 10:1 to give 1-[N-benzyloxycarbonyl-(S)-alanyl]octahydroindole-2(R)-carboxylic acid, ethyl ester, a colorless oil $[\alpha]_D^{26}+22.0°$ (ethanol) and 1-[N-benzyloxycarbonyl-(S)alanyl]octahydroindole-2(S)-carboxylic acid, ethyl ester, a colorless oil $[\alpha]_D^{26}-96.4°$ (ethanol).

C. To a solution of 3.22 g of 1-[N-benzyloxycarbonyl-(S)-alanyl]octahydroindole-2(S)-carboxylic acid, ethyl ester in 150 ml of methanol, add 20 ml of 2.5N sodium hydroxide and stir the mixture at room temperature for 18 hours. Concentrate the mixture under nitrogen, dilute the residue with ice-water and then make the mixture acidic with concentrated hydrochloric acid. Extract the aqueous solution with ethyl acetate and dry the organic phase over magnesium sulfate. Concentrate the organic phase and place it on a column of silica gel (500 g., 60–200 mesh). Elute with chloroform:glacial acetic acid 9:1 to give 1- [N-benzyloxycarbonyl-(S)-alanyl]octahydroindole-2(S)-carboxylic acid, a white solid $[\alpha]_D^{26}62.1°$ (ethanol), m.p. 58.60°.

Dissolve 1.70 g of 1-[N-Benzyloxycarbonyl-(S)-alanyl]octahydroindole-2(S)-carboxylic acid in 100 ml of methanol. Add 0.40 g 10% palladium-on-charcoal and hydrogenate the mixture at atmospheric pressure. Filter the mixture and concentrate in vacuo to give 1-[(S)-alanyl ]octahydroindole-2(S)-carboxylic acid, a white solid $[\alpha]_D^{26}-18.5°$ (ethanol), m.p. 163°–165°.

E. Dissolve 1-[(S)-alanyl ]octahydroindole-2(S)-carboxylic acid (prepared in paragraph D of this example) in 100 ml of absolute methanol. Add 1.10 g 2-oxo-4-phenylbutyric acid, ethyl ester and 20 ml of 3 Angstrom molecular sieve pellets, and stir the resulting mixture at room temperature for eighteen hours. Filter the reaction mixture and treat the filtrate with 0.68 g sodium cyanoborohydride at room temperature for two hours. Concentrate the mixture under nitrogen and dilute the oil with dilute hydrochloric acid and stir at room temperature for one hour. Absorb the aqueous solution on 200 ml of a XAD-2 (Rohm & Haas-Co. resin). Elute the resin with 2000 ml of water and then with 2000 ml of methanol. Concentrate the methanol solution and place the residue on a column of silica gel (400 g, 60–200 mesh) and elute with chloroform:isopropanol: 7% ammonium hydroxide 1:1:1 (organic layer) to give 1-[N-(1-methoxycarbonyl-3-phenyl propyl)-(S)-alanyl]octahydroindole-2(S)-carboxylic acid, a white solid $[\alpha]_D^{26}-45.3°$ (ethanol), m.p. 71°–73°.

EXAMPLE 2

1-[N-(1-Carboxy-3-phenylpropyl)-(S)-alanyl]octahydroindole-2(S)-carboxylic acid

To a solution of 1-[N-(1-carbomethoxy-3-phenylpropyl)-(S)-alanyl]]octahydroindole-2(S)-carboxylic acid (prepared as described in Example 1) in methanol, add 2.5N sodium hydroxide. After three hours, concentrate the reaction mixture and absorb it on an XAD-2 resin column and elute with water and then with methanol, Concentrate the methanol eluant to give a residue and absorb this residue on a silica gel column elute with chlorform:methanol: 14% ammonium hydroxide 1:1:1, Concentrate the desired eluant fractions to obtain the title compound.

EXAMPLE 3

1-[N-(1-Carboethoxy-3-p-chlorophenylpropyl)-(S)-alanyl]octahydroindole-2-(S)-carboxylic acid React 1-[(S)-alanyl]octahydroindole-2(S)-carboxylic acid (prepared as described in Example 1) and ethyl p-chlorophenyl-2-oxobutyrate with sodium cyanoborohydride as described in Example 1E ( ethanol solvent) to obtain the title compound.

EXAMPLE 4

1-[N-(1-Carboxy-3-p-chlorophenylpropyl)-(S)-alanyl-]octahydroindole-2(S)-carboxylic acid Treat the ester (prepared as described in Example 3) with sodium hydroxide in methanol as described in Example 2 to yield the title compound.

EXAMPLE 5

1-[N-(1-Carboxy-2-phenylethyl)-(S)-alanyl]octahydroindole-2(S)-carboxylic acid

To a mixture of 1-[(S)-alanyl]octahydroindole-2(S)-carboxylic acid (prepared as described in Example 1) and phenylpyruvic acid in methanol water at a pH of about 7, at room temperature, add sodium cyanoborohydride. Upon completion of the reaction, absorb the residue on a XAD-2 resin and elute with methanol followed by further purification by elution from silica gel using chloroform:methanol: 14% ammonium hydroxide 1:1:1 to isolate the title compound.

EXAMPLE 6

1-[N-(1-Aminocarbonyl-3-phenylpropyl)-(S)-alanyl]octahydroindole-2(S)-carboxylic acid React 1-[(S)-alanyl]octahydroindole-2(S)-carboxylic acid (preparable as described in Example 1) and 2-oxo-4-phenylbutyramide and sodium cyanoborohydride to obtain the title compound as described in Example 5.

EXAMPLE 7

1{N-[1-Carboxy-3-(3-indolyl)propyl]-(S)-alanyl}octahydroindole-2(S)-carboxylic acid Condense 1-[(S)-alanyl]octahydroindole-2(S)-carboxylic acid (preparable as described in Example 1) and 4-(3-indolyl)-2-oxobutyric acid with sodium cyanoborohydride, using the procedure described in Example 5 to yield the title compound.

EXAMPLE 8

1-{N-[1-Carboethoxy-2-(3-indolyl)ethyl]-(S)-alanyl}octahydroindole-2(S)-carboxylic acid As described in Example 1, react 1-[(S)-alanyl]octahydroindole-2(S)-carboxylic acid and ethyl indole-3-pyruvate with sodium cyanoborohydride to obtain the title compound.

EXAMPLE 9

1-[N-(1-Carboxy-2-phenoxyethyl)-(S)-alanyl]octahydroindole-2(S)-carboxylic acid

As described in Example 5, condense 1-[(S)-alanyl]octahydroindole-2(S)-carboxylic acid (prepared as described in Example 1) and phenoxypyruvic acid (preparable from ethyl phenoxyacetate and diethyl oxalate, followed by acid catalysed hydrolysis and decarboxylation) with sodium cyanoborohydride to obtain the title compound.

EXAMPLE 10

1-[N-(1-Carboethoxy-2-phenoxyethyl)-(S)-alanyl]octahydroindole-2(S)-carboxylic acid React 1-[(S)-alanyl]octahydroindole-2(S)-carboxylic acid (preparable as described in Example 1) and ethyl phenoxypyruvate, (prepared from esterification of phenoxypyruvic acid as described in Example 9) with sodium cyanoborohydride as described in Example 1 to give the title compound.

EXAMPLE 11

1-[N-(1-Carboxy-2-phenylthioethyl)-(S)-alanyl]octahydroindole-2(S)-carboxylic acid Condense 1-[(S)-alanyl]octahydroindole-2(S)-carboxylic acid (prepared as described in Example 1) and phenylthiopyruvic acid (preparable from ethyl phenylthioacetate and diethyl oxalate, followed by acid catalyzed hydrolysis and decarboxylation) with sodium cyanoborohydride as described in Example 5 to yield the title compound.

EXAMPLE 12

1-[N-(1-Carboxyethyl)-(S)-alanyl]octahydroindole-2(S)-carboxylic acid

As described in Example 5, react 1-[(S)-alanyl]octahydroindole-2(S)-carboxylic acid (prepared as described in Example 1) and pyruvic acid with sodium cyanoborohydride to obtain the title compound.

EXAMPLE 13

1-[N-(1-Carboxy-2-cyclohexylethyl)-(S)-alanyl]octahydroindole-2-(S)-carboxylic acid Condense 1-[(S)-alanyl]octahydroindole-2(S)-carboxylic acid (prepared as described in Example 1) and 3-cyclohexyl-2-oxopropionic acid with sodium cyanoborohydride as described in Example 5 to obtain the title compound,

EXAMPLE 14

1-[N-(1-Carboxy-5-methylhexyl-(S)-alanyl]octahydroindole-2(S)-carboxylic acid

To 1-[(S)-alanyl]octahydroindole-2(S)-carboxylic acid (prepared as described in Example 1) and 4-methyl-2-oxopentanoic acid add sodium cyanoborohydride using the procedure described in Example 5 to obtain the title compound,

EXAMPLE 15

1-[N-(1,3-Dicarboxypropyl)-(S)-alanyl]octahydroindole-2(S)-carboxylic acid

As described in Example 5, treat 1-[(S)-alanyl]octahydroindole-2(S)-carboxylic acid (prepared as described in Example 1) and 2-oxoglutaric acid with sodium cyanoborohydride to isolate the title compound.

EXAMPLE 16

1-[N-(1-Carboethoxy-3-phenylpropyl)-(S)-alanyl]-decahydroquinoline-2(S)-carboxylic acid Use ethyl decahydroquinoline-2-carboxylate (prepared by hydrogenation of quinoline-2-carboxylic acid in glacial acetic acid with platinum oxide followed by esterfication in ethanol) in place of ethyl octahydroindole-2-carboxylate in Example 1B. Continue the sequence of reactions described in Example 1 through Example 1E to obtain the title compound.

EXAMPLE 17

1-[N-(1-Carboxy-3-phenylpropyl)-(S)-alanyl]decahydroquinoline-2(S)-carboxylic acid As described in Example 2, treat 1-[N-(1-carboethoxy-3-phenylpropyl)-(S)-alanyl]decahydroquinoline-2-carboxylic acid (prepared as described in Example 16) with sodium hydroxide to obtain the title compound.

EXAMPLE 18

2-[N-(1-Carboethoxy-3-phenylpropyl)-(S)-alanyl]octahydroisoindole-1(S)-carboxylic acid A. Heat cis-octahydroisoindole (prepared by reduction of cis-hexahydrophthalimide in tetrahydrofuran with lithium aluminum hydride) and mercuric acetate in 10% aqueous acetic acid under reflux for twenty hours to give cis-hexahydro-$\Delta^1$-isoindole. Dissolve this compound in water and treat with potassium cyanide followed by 2N hydrochloric acid at 0° for two hours and at room temperature for twenty hours to give 1-cyano-cis-octahydroisoindole, Heat this cyano compound in 6N hydrochloric acid under reflux for 6 hours followed by concentration of the reaction mixture and absorption of the residue on an XAD-2 resin column, Elute with methanol to obtain cis-octahydroisoindole-1-carboxylic acid, B. Use ethyl cis-octahydroisoindole-1-carboxlyate (prepared by esterification with ethanol of the acid prepared in paragraph A next above) in place of ethyl octahydroindole-2-carboxylate in Example 1B through 1E to give the title compound.

EXAMPLE 19

2-[N-(1-Carboxy-3-phenylpropyl)-(S)-alanyl]octahydroisoindole-1(S)-carboxylic acid As described in Example 2 treat N-(1-carboethoxy-3-phenylpropyl-(S)-alanyl]octahydroisoindole-1(S)-carboxylic acid (prepared as described in Example 18) with sodium hydroxide to obtain the title compound.

EXAMPLE 20

1-[N-(1-Carboethoxy-3-phenylpropyl)-(S)-alanyl]octahydrocyclopenta[b]pyrrole-2(S)-carboxylic acid

A. Substitute octahydrocyclopenta [b]pyrrole (prepared by reduction of 2-ketooctahydrocyclopenta[b]pyrrole in tetrahydrofuran with lithium aluminum hydride) for octahydroisoindole in Example 18A to obtain octahydrocylopenta[b]pyrrole-2-carboxylic acid.

B. Use ethyl octahydrocyclopenta[b]pyrrole-2-carboxylate (prepared by esterification with the ethanol of the acid prepared as described in paragraph A) in place of ethyl octahydroindole-2-carboxylate in the procedure described in paragraphs B through E of Example 1 to give the title compound.

EXAMPLE 21

1-[N-(1-Carboxy-3-phenylpropyl)-(S)alanyl]octahydrocyclopenta[b]pyrrole-2(S)-carboxylic acid

As described in Example 2, hydrolyze the ester (prepared as described in Example 20) with sodium hydroxide to obtain the title compound.

EXAMPLE 22

5-[N-(1-Carboethoxy-3-phenylpropyl)-(S)-alanyl-2,2-dimethyloctahydro-1,3-dioxolo[4,5-c]pyrrole-4(S)-carboxylic acid

Heat 1-benzyloxycarbonyl-3,4-dihydroxy-(S)-proline preparable from reaction of 3,4-dihydroxy-(S)-proline in 2N sodium hydroxide with benzyl chloroformate in ether] with 2,2-dimethoxy propane in dimethylformamide and p-toluenesulfonic acid to obtain 5-benzyloxycarbonyl-2,2-dimethyloctahydro-1,3-dioxolo[4,5-c)pyrrole-4(S)-carboxylic acid. Hydrogenate this compound in methanol with palladium on carbon to give 2,2-dimethyloctahydro-1,3-dioxolo [4,5-c]pyrrole-4(S)-carboxylic acid. React this compound with N-benzyloxycarbonyl-(S)-alanine, N-hydroxysuccinimide ester as described in Example 1B-E to isolate the title compound.

EXAMPLE 23

7-[N-(1-Carboxy-3-phenylpropyl)-(S)-alanyl]-1,4-dithia-7-azaspiro[4.4]nonane-8(S)-carboxylic acid

A. Dissolve 7.0 g of 1-benzyloxycarbonyl-4-keto-(S)proline methyl ester in 75 ml of glacial acetic acid. Add 0.7 g of p-toluenesulfonic acid and 2.8 g of 1,2-ethanedithiol and heat under reflux with stirring for eighteen hours. Add the reaction mixture to saturated sodium bicarbonate solution and extract with ethyl acetate. Dry the organic layer over magnesium sulfate and concentrate it. Place the residue on a column of silica gel (300 g, 60–200 mesh) and elute with hexane:ethyl acetate (1:1) to give 7-benzyloxcarbonyl-1,4-dithia-7-azaspiro [4.4]nonane-8 (S) -carboxylic acid, methyl ester, a yellow oil having $[\alpha]_D^{26} -12.6°$ (dioxane).

B. Dissolve 3.0 g of 7-benzyloxycarbonyl-1,4-dithia-7-azaspiro[4.4]nonane-8(S)-carboxylic acid, methyl ester in 20 ml of 20% hydrobromic acid in glacial acetic acid and stir the mixture at room temperature for two hours. Add the mixture dropwise to diethyl ether at 0°–5° C. to give 1,4-dithia-7-azaspiro [4.4]nonane-8(S)-carboxylic acid, methyl ester hydrobromide, a brown solid m.p. 156°–158°.

C. Dissolve the 1,4-dithia-7-azaspiro[4.4]nonane-8-(S)-carboxylic acid, methyl ester, hydrobromide from paragraph B in 0.1N NaOH and extract with ethyl acetate. Dry the organic layer over magnesium sulfate and concentrate in vacuo to give 1,4-dithia-7-azaspiro [4.4]nonane-8(S)-carboxylic acid, methyl ester (1.35 g). Dissolve the latter in 100 ml of ethyl acetate and treat with 2.07 g of N-benzyloxycarbonyl-(S)-alanine, N-hydroxysuccinimide ester. Stir the reaction mixture at room temperature for eighteen hours and concentrate in vacuo. Place the residue on a column of silica gel (300 g, 60–200 mesh) and elute with hexane:ethyl acetate 4:1 to obtain 7-[N-benzyloxy-carbonyl-(S)-alanyl]-1,4-dithia-7-azaspiro[4.4 ]nonane-8(S)-carboxylic acid, methyl ester, a yellow oil $[\alpha]_D^{26} -14.8°$ (ethanol).

D. Dissolve 1.05 g of 7-[N-benzyloxycarbonyl-(S)-alanyl]-1,4-dithia-7-azaspiro[4.4]nonane-8(S)-carboxylic acid, methyl ester in 100 ml of methanol. Add 10 ml of 2.5N sodium hydroxide and stir the mixture at room temperature for sixteen hours. Concentrate the mixture under nitrogen, dissolve the oil in 0.1N sodium hydroxide and dilute with ice water. Extract the aqueous solution with ethyl acetate. Acidify the aqueous solution with concentrated hydrochloric acid and then extract with ethyl acetate. Dry the organic phase over magnesium sulfate and concentrate it. Place the residue on a column of silica gel (100 g, 60–200 mesh) and elute with chloroform:glacial acetic acid 19:1 to obtain 7-[N-benzyloxycarbonyl-(S) -alanyl]-1,4-dithia-7-azaspiro-[4.4]nonane-8(S)-carboxylic acid, $[\alpha]_D^{26} -15.8°$ (ethanol).

E. Dissolve 1.4 g of 7-[N-benzyloxycarbonyl-(S)-alanyl]-1,4-dithia-7-azaspiro[4.4]nonane-8(S)-carboxylic acid in 20 ml of 20% hydrobromic acid in glacial acetic acid and stir the mixture at room temperature for 2 hours. Add the mixture dropwise to diethyl ether at 0°–5° C. to give 7-[(S)-alanyl]- 1,4-dithia-7-azaspiro[4.4]nonane-8(S)-carboxylic acid hydrobromide which is used immediately in the process described in paragraph F below.

F. Dissolve the 7-[(S)-alanyl]-1,4-dithia-7-azaspiro-[4.4]nonane-8(S)-carboxylic acid, hydrobromide (prepared in paragraph E next above) in 100 ml of absolute methanol. Add 0.5 g of 2-oxo-4-phenylbutyric acid, ethyl ester and 10 ml of 3° A. molecular sieve pellets and stir the reaction mixture at room temperature for eighteen hours. Filter the reaction mixture and treat the filtrate with 0.30 g of sodium cyanoborohydride at room temperature for two hours. Concentrate the mixture under nitrogen and dilute the oil with 5% hydrochloric acid to pH 2 to 4 and stir at room temperature for one hour. Adjust the pH of the solution to pH 8 with 2.5N sodium hydroxide solution and absorbed the solution in 150 ml of a XAD-2 resin. Elute the resin with 800 ml of water and then with 800 ml of methanol. Concentrate the methanol solution, place the residue on a column of silica gel (100 g, 60–200 mesh) and elute with chloroform:isopropanol: 7% ammonium hydroxide 1:1:1 (organic layer) to obtain 7-[N-(1-carboethoxy-3-phenylpropyl)-(S)-alanyl]-1,4-dithia-7-azaspiro[4.4]nonane-8(S)-carboxylic acid, a white solid, m.p. 56°–60° C., $[\alpha]_D^{26} -25.5°$ (ethanol).

EXAMPLE 24

7-[N-(1-Carboxy-3-phenylpropyl)-(S)-alanyl]-1,4-dithia-7-azaspiro[4.4]nonane-8(S)-carboxylic acid

Hydrolyze 0.18 g of 7-[N-(1-carboethoxy-3-phenylpropyl)-(S)-alanyl]-1,4-dithia-7-azaspiro [4.4]nonane-8 (S) -carboxylic acid (prepared as described in Example 23) in 600 ml of methanol with 10 ml of 2.5N sodium hydroxide, concentrate the reaction mixture and absorb it on an XAD-2 resin column and elute with water and then with methanol. Concentrate the methanol eluant to give a residue and absorb this residue on a silica gel column (100 g, 60–200 mesh). Elute the column with chloroform:methanol: 14% ammonium hydroxide 1:1:1 and concentrate the desired eluant fractions to obtain the title compound.

EXAMPLE 25

7-[N-(1-Carbomethoxy-3-methylthiopropyl)-(R,S)-alanyl]-1,4-dithia-7-azaspiro[4.4]nonane-8(S)-carboxylic acid A. Couple 1,4-dithia-7-azaspiro[4.4]nonane-8(S)-carboxylic acid, methyl ester (prepared as described in Example 23) with pyruvic acid using dicyclohexylcarbodiimide and triethylamine in dioxane to yield, after isolation and hydrolysis of the ester, 7-pyruvoyl-1,4-dithia-7-azaspiro-[4.4]nonane-8(S)-carboxylic acid.

B. Condense 7-pyruvoyl-1,4-dithia-7-azaspiro[4.4]nonane-8(S)-carboxylic acid and (S)-methionine, methyl ester with sodium cyanoborohydride in methanol at pH 7 for three days at room temperature followed by chromatography on a XAD-2 resin column, using methanol as eluant, to obtain the title compound.

EXAMPLE 26

7-[N-(1-Carboxy-3-methylthiopropyl)-(R,S)-alanyl]-1,4-dithia-7-azaspiro[4.4]nonane-8(S)-carboxylic acid Treat 7-[N-(1-carbomethoxy-3-methylthiopropyl)-(R,S)alanyl]-1,4-dithia-7-azaspiro[4.4]nonane-8(S)-carboxylic acid, (prepared as described in Example 25) with sodium hydroxide in methanol as described in Example 24 to yield the title compound.

EXAMPLE 27

7-{N-[1-Carbomethoxy-2-(3-indolyl)ethyl]-(R,S)-alanyl}-1,4-dithia-7-azaspiro[4.4]nonane-8(S)-carboxylic acid Use 7-pyruvoyl-1,4-dithia-7-azaspiro[4.4]nonane-8(S)-carboxylic acid (prepared as described in Example 25) and condense with tryptophan methyl ester in the presence of sodium cyanoborohydride using the method described in Example 25 to obtain the title compound.

EXAMPLE 28

7-{N-[1-Carboxy-2-(3-indolyl)ethyl]-(R,S)alanyl}-1,4-dithia-7-azaspiro-[4.4]nonane-8(S)-carboxylic acid Hydrolyze 7-{N-[1-carbomethoxy-2-(3-indolyl)ethyl]-(R,S)-alanyl}-1,4-dithia-7-azaspiro[4.4]nonane-8(S)-carboxylic acid (prepared as described in Example 27) with sodium hydroxide as described in Example 24 to yield the title compound.

EXAMPLE 29

7-{N-[1-Carbomethoxy-2-(1H-imidazol-4-yl)ethyl]-(R,S)-alanyl}-1,4-dithia-7-azaspiro[4.4]nonane-8(S)-carboxylic acid As described in Example 25, react 7-pyruvoyl-1,4-dithia-7-azaspiro[4.4]nonane-8(S)-carboxylic acid (prepared as described in Example 25) and (S)-histidine, methyl ester in the presence of sodium cyanoborohydride to obtain the title compound.

EXAMPLE 30

7-{N-[1-carboxy-2-(1H-imidazol-4-yl)ethyl]-(R,S)-alanyl}-1,4-dithia-7-azaspiro [4.4]nonane-8(S)-carboxylic acid Treat 7-{N-[1-carbomethoxy-2-(1H-imidazolyl-4-yl)-ethyl]-(R,S)-alanyl}-1,4-dithia-7-azaspiro[4.4]nonane-8(S)carboxylic acid (prepared as described in Example 29) with sodium hydroxide as described in Example 24 to yield the title compound.

EXAMPLE 31

7-[N-(1-Carboethoxy-3-phenylpropyl)glycyl]-1,4-dithia-7-azaspiro[4.4]nonane-8(s)-carboxylic acid A. As described in Example 23, react 1-benzyloxycarbonyl-4-keto-(S)-proline, ethyl ester (prepared from the acid by esterification in ethanol) with 1,2-ethanedithiol to obtain 7-benzyloxycarbonyl-1,4-dithia-7-azaspiro [4.4]nonane-8(S)carboxylic acid, ethyl ester, a yellow oil $[\alpha]_D^{26} -21.0°$ (ethanol).

B. Convert 2.22 g of 7-benzyloxycarbonyl-1,4-dithia-7-azaspiro[4.4]nonane-8(S)-carboxylic acid, ethyl ester (prepared as described in paragraph A) to 1,4-dithia-7-azaspiro-[4.4]nonane-8(S)-carboxylic acid, ethyl ester as described in Example 23 and couple this compound with 1.5 g of N-benzyloxycarbonylglycine, N-hydroxysuccinimide ester as described in Example 23 to yield 7-(N-benzyloxycarbonylglycyl)-1,4-dithia-7-azaspiro[4.4]nonane-8(S)-carboxylic acid, ethyl ester, a yellow oil $[\alpha]_D^{26} -21.0°$.

C. Hydrolyze 1.43 g of 7-(N-benzyloxycarbonylglycyl)-1,4-dithia-7-azaspiro [4.4]nonane-8(S) -carboxylic acid, ethyl ester (prepared as described in paragraph B next above) with sodium hydroxide as described in Example 23 to obtain 7-(N-benzyloxycarbonylglycyl)-1,4-dithia-7-azaspiro[4.4]nonane-8(S)-carboxylic acid, a colorless oil, $[\alpha]_D^{26} -7.9°$.

D. Treat 0.95 g of the acid obtained in the process described in paragraph C next above with 20% hydrobromic acid in glacial acetic acid as described in Example 23 to obtain 7-glycyl-1,4-dithia-7-azaspiro [4.4]nonane-8(S)-carboxylic acid, hydrobromide $[\alpha]_D^{26} 18.7°$.

E. As described in Example 23, couple 0.76 g of 7-glycyl-1,4-dithia-7-azaspiro [4.4]nonane-8(S)-carboxylic acid, hydrobromide (prepared as described in paragraph D next above) with 0.50 g of 2-oxo-4-phenylbutric acid, ethyl ester to obtain 7-[N-(1-carboethoxy-3-phenylpropyl)glycyl]-1,4-dithia-7-azaspiro[4.4]nonane-8(S)-carboxylic acid.

EXAMPLE 32

7-[N-(1-Carboxy-3-phenylpropyl)glycyl]-1,4-dithia-7-azaspiro[4.4]nonane-8(S)-carboxylic acid As described in Example 24, hydrolyze 7-[N-(1-carboethoxy-3-phenylpropyl )glycyl]-1,4-dithia-7-azaspiro[4.4 ]nonane-8(S)-carboxylic acid (prepared as described in Example 31) with sodium hydroxide to give the title compound.

EXAMPLE 33

7-[N-(1-Carboethoxy-3-phenylpropyl)-(S)-alanyl]-1,4-dithia-7-azaspiro[4.5 ]decane-8(S)-carboxylic acid A. Dissolve 1-benzyloxycarbonyl-5-hydroxy-(S)-pipecolic acid (prepared from 5-hydroxy-(S)-pipecolic acid in 2N sodium hydroxide solution treated with benzylchlorformate in diethyl ether) in acetone and treat with Jones reagent to obtain 1-benzyloxycarbonyl-5-keto-(S)-pipecolic acid. Then esterify in methanol to give the respective methyl ester.

B. Substitute 1-benzyloxycarbonyl-5-keto-(S)-pipecolic acid, methyl ester as the keto-ester in Example 23 and follow the procedure described to obtain the title compound.

EXAMPLE 34

7-[N-(1-Carboxy-3-phenylpropyl)-(S)-alanyl]-1,4-dithia-7-azaspiro[4.5]decane-8(S)-carboxylic acid Hydrolyze 7-[N-(1-carboethoxy-3-phenylpropyl)-(S)-alanyl]-1,4-dithia-7-azaspiro[4.5]decane-8(S)-carboxylic acid (prepared as described in Example 33) with sodium hydroxide and isolate the title compound using the procedure described in Example 24.

EXAMPLE 35

1-[N-(1-Carboethoxy-3-phenylpropyl)-(S)-alanyl]-1-azaspiro[4.4]-nonane-2(S)-carboxylic acid A. Condense nitrocyclopentane (prepared from bromocyclopentane and sodium nitrite) and acrolein in tetrahydrofuran in the presence of sodium hydride to obtain 3-(1-nitrocyclopentyl)propionaldehyde. Treat this aldehyde with p-toluenesulfonic acid in methanol and isolate 3-(1-nitrocylopentyl) propionaldehyde dimethyl acetal. Hydrogenate this compound with Raney nickel. Isolate 3-(1-aminocyclopentyl)propionaldehyde dimethylacetal and dissolve in aqueous acetone in the presence of p-toluenesulfonic acid and heat under reflux, followed by addition of toluene and azeotrope the mixture to give 1-azaspiro[4.4]-$\Delta^1$-nonane.

B. Substitute 1-azaspiro[4.4]-$\Delta^1$-nonane (from paragraph A) for cis-hexahydro-$\Delta^1$-isoindole in Example 18A to obtain 1-azaspiro[4.4]nonane-2-carboxylic acid.

C. Use 1-azaspiro[4.4]nonane-2-carboxylic acid, ethyl ester prepared by esterification of the acid (obtained as described in paragraph B) in methanol in place of octahydroindole-2-carboxylic acid, ethyl ester in Example 1B through 1E to obtain the title compound.

EXAMPLE 36

2-[N-(1-Carboethoxy-3-phenylpropyl)-(S)-alanyl]-2-azaspiro[4.4]-nonane-3(S)-carboxylic acid A. Reduce 2-(1-cyanocyclopentylacetaldehyde diethyl acetal (preparable from 3-cyanopropionaldehyde diethyl acetal and 1,4-dibromobutane in tetrahydrofuran in the presence of sodium hydride) with lithium aluminum hydride to yield 2-(1-aminomethylcyclopentyl)acetaldehyde, diethyl acetal. Dissolve this compound in aqueous acetone in the presence of p-toluenesulfonic acid and heat under reflux, followed by addition of toluene and azeotrope the mixture to give $\Delta^2$-2-azaspiro[4.4]nonane.

B. Substitute $\Delta^2$-2-azaspiro [4.4]nonane (prepared as described in paragraph A for cis-hexahydro-$\Delta$996 1-isoindole in Example 18A to yield 2-azaspiro[4.4]nonane-3-carboxylic acid.

C. As described in Example 1B through 1E, substitute 2-azaspiro [4.4]nonane-3-carboxylic acid, ethyl ester (preparable by esterfication of the acid from paragraph B in ethanol) for octahydroindole-2-carboxylic acid, ethyl ester to obtain the title compound.

EXAMPLE 37

1-[N-(1-Carboethoxy-3-phenylpropyl)-(S)-alanyl]-4(R,S)-[2-(1,3-dithianyl)]-(S)-proline A. React 4(R,S)-cyano-(S)-proline, methyl ester (prepared from reaction of 4(R)-tosyloxy-(S)-proline, methyl ester in acetonitrile with potassium cyanide and dibenzo-18-crown-6) with 2-methyl-2,4-pentanediol in cold concentrated sulfuric acid to yield 4-[2-(4,6,6-trimethyl-5,6-dihydro-4H-1,3-oxazinyl)]-(S)-proline, methyl ester. Reduce this compound with sodium borohydride in aqueous methanol at pH 2–4 at 0°, and then hydrolyze with aqueous oxalic acid to yield 4-formyl-(S)-proline, methyl ester.

B. Combine 4-formyl-(S)-proline, methyl ester (prepared as described in paragraph A) and 1,3-propanedithiol by the procedure described in Example 23 to obtain the title compound.

EXAMPLE 38

N-[N-(1-Carbomethoxy-3-phenylpropyl)-(S)-alanyl]-N-cyclohexyl-(S)-alanine

Substitute N-cyclohexyl-(R,S)-alanine, ethyl ester (prepared from cyclohexylamine and ethyl bromoacetate) for ethyl octahydroindole-2-carboxylate in Example 1B and continue the sequence through to 1E to obtain the title compound.

EXAMPLE 39

N-{N-[(1-Carbomethoxy-3-phenylpropyl)-(S)-alanyl]}-N-(2,2-diethoxy)ethyl-(S)-alanine Use N-(2,2-diethoxy)ethyl-(S)-alanine, methyl ester (prepared from (S)-alanine, methyl ester, hydrochloride and bromoacetaldehyde diethylacetal) for ethyl octahydroindole-2-carboxylate in Example 1B and continue the sequence through to 1E to isolate the title compound.

EXAMPLE 40

N-[N-(1-Carboethoxy-3-phenylpropyl)-(S)-alanyl-N-[2-(1,3-dithianyl)methyl]-(S)-alanine Combine N-(2,2-diethoxy)ethyl-(S)-alanine, methyl ester (prepared as described in Example 39) and 1,3-propanedithiol as described in Example 23A and continue the sequence as outlined to yield the title compound.

EXAMPLE 41

1-[N-(1-Ethoxycarbonyl-3-phenylpropyl)-(S)-alanyl-]azacyclooctane-2-(S)-carboxylic acid A. To a solution of 9.4 g of ethyl azacyclooctane-2-carboxylate in 400 ml of ethyl acetate add 17.0 g of N-benzyloxycarbonyl-(S)-alanine, N-hydroxysuccinimide ester. Stir the reaction mixture at room temperature for 20 hours and concentrate it in vacuo to give 1-[N-benzyloxycarbonyl-(S)-alanyl]azacyclooctane-2(R,S)-carboxylic acid, ethyl ester, as a colorless oil.

B. To a solution of 3.09 g of 1-[N-benzyloxycarbonyl-(S)-alanyl]azacyclooctane-2(R,S)-carboxylic acid, ethyl ester in 150 ml methanol, add 20 ml of 2.5 N sodium hydroxide and stir the mixture at room temperature for 18 hours. Concentrate the mixture under nitrogen, dilute the residue with ice-water and then make the mixture acidic with concentrated hydrochloric acid. Extract the aqueous solution with ethyl acetate and dry the organic phase over magnesium sulfate. Concentrate the organic phase to give a white residue. Place the residue on a column of silica gel (1000 ml, 60–200 mesh) and elute with chloroform:isopropanol:7% NH$_4$OH (organic phase) to give 1-[N-benzyloxycarbonyl-(S)-alanyl]azacyclooctane-2(R)-carboxylic acid and 1-[N-benzyloxycarbonyl-(S)-alanyl]azacyclooctane-2(S)-carboxylic acid, as colorless oils.

C. Dissolve 1.59 g of 1-[N-benzyloxycarbonyl-(S)-alanyl]-azacyclooctane-2(S)-carboxylic acid in 100 ml of methanol. Add 0.40 g 10% palladium-on-charcoal and hydrogenate the mixture at atmospheric pressure. Filter the mixture and concentrate in vacuo to give 1-[(S)-alanyl]azacyclooctane-2(S)-carboxylic acid.

D. Dissolve 1-[(S)-alanyl]azacyclooctane-2(S)-carboxylic acid (prepared in paragraph C of this example) in 100 ml of absolute ethanol. Add 1.10 g 2-oxo-4-phenylbutyric acid, ethyl ester and 20 ml of 3 Angstrom molecular sieve pellets, and stir the resulting mixture at room temperature for eighteen hours. Filter the reaction mixture and treat the filtrate with 0.68 g sodium cyanoborohydride at room temperature for two hours. Concentrate the mixture under nitrogen and dilute the oil with dilute hydrochloric acid and stir at room temperature for one hour. Absorb the aqueous solution on 200 ml of a XAD-2 (Rohm & Hass Co.) resin. Elute the resin with 2000 ml of water and then with 2000 ml of methanol. Concentrate the methanol solution and place the residue on a column of silica gel (400 g, 60–200 mesh) and elute with chloroform:isopropanol: 7% ammonium hydroxide 1:1:1 (organic layer) to give 1-[N-(1-ethoxycarbonyl-3-phenylpropyl)-(S)-alanyl]azacyclooctane-2(S)-carboxylic acid.

EXAMPLE 42

1-[N-(1-Carboxy-3-phenylpropyl)-(S)-alanyl]azacyclooctane-2(S)-carboxylic acid

To a solution of 1-[N-(1-ethoxycarbonyl-3-phenylpropyl) (S)-alanyl]azacyclooctane-2(S)-carboxylic acid (prepared as described in Example 41) in ethanol, add 0.25N sodium hydroxide. After three hours, concentrate the reaction mixture and absorb it on an XAD-2 resin column and elute with water and then with methanol. Concentrate the methanol eluant to give a residue and absorb this residue on a silica gel column and elute with chloroform:methanol: 14% ammonium hydroxide 1:1:1. Concentrate the desired eluant fractions to obtain the title compound.

EXAMPLE 43

1-[N-(Ethoxycarbonyl-3-phenylpropyl)-(S)-alanyl]azacyclononane-2(S)-carboxylic acid According to the method of Example 41, starting with ethyl azacyclononane-2-carboxylate, prepare the title compound.

EXAMPLE 44

1-[N-α-(1-Ethoxycarbonyl-3-phenylpropyl)-(S)-lysyl]azacyclodecane 2(S)-carboxylic acid According to the method of Example 41A, combine 10.6 g ethyl azacyclodecane-2-carboxylate with 25.4 g N-α-t-butoxycarbonyl ε-carbobenzyloxy-L-lysine, N-hydroxysuccinimide ester to produce ethyl 1-[N-α-t-butoxycarbonyl-N-ε-carbobenzyloxy-(S)-lysyl]azacyclodecane-2(S)-carboxylate.

B. Dissolve the above product in acetonitrile-aqueous NaOH (pH 13), stir for one hour, concentrate, neutralize to pH 8 and extract with ethyl acetate. Dry the ethyl acetate, and add an equal volume of 4N hydrogen chloride in the same solvent. Concentrate, and triturate the residue with ether to give a solid, 1-[N-ε-carbobenzyloxy-(S)-lysyl]azacyclodecane-2-(S)-carboxylic acid, hydrochloride.

C. Combine 2.4 g of the above product with 0.8 g sodium acetate in 100 ml ethanol. Add 4.0 g ethyl 2-oxo-4-phenylbutyrate and 0.63 g NaCNBH$_3$. After four hours, work up as in Example 41D. Combine the desired chromatography fractions in 100 ml ethanol with 0.5 g Pd/C and shake under 3 atm. hydrogen for six hours. Filter the catalyst and remove the solvent to obtain the title compound.

EXAMPLE 45

4-[N-(1-Ethoxycarbonyl-3-phenylpropyl)-(S)-alanyl]-4-aza-1-thiacyclononane-5(S)-carboxylic acid A. According to the method of example 41, parts A and B, convert ethyl 4-aza-1-thiacyclononane-5-carboxylate into 4-[N-benzyloxycarbonyl-(S)-alanyl]-4-aza-1-thiacyclononane-5(S)-carboxylic acid.

B. Dissolve 2.4 g of the above acid in 20 ml of 20% hydrobromic acid in glacial acetic acid. Stir at room temperature on hour and dilute slowly with ether to obtain 4-[(S)-alanyl]-4-aza-1-thiacyclononane-5(S)-carboxylic acid, hydrobromide salt.

C. Dissolve the above salt in 100 ml ethanol and add sodium carbonate (0.30 g) and ethyl 2-oxo-4-phenylbutyrate (1.1 g). Add 10 ml of 3 Angstrom molecular sieve pellets and stir twenty hours. Filter and add sodium cyanoborohydride (0.60 g). Stir four hours, concentrate, add 10 ml 1N hydrochloric acid and stir one hour. Place on 200 ml of XAD-2 resin, wash with 2.0 liters of water, and elute with 2.0 liters of methanol. Concentrate the methanol and place on a column of silica gel (0.5 kg). Elute with chloroform:ethanol:7% ammonium hydroxide 1:1:1 to obtain 4-[N-(1-ethoxycarbonyl-3-phenylpropyl-(S)-alanyl]-4-aza-1-thiacyclononane-5-(S)-carboxylic acid.

EXAMPLE 46

5-[N-(1(S)-carboxy-5-aminopentyl)-(R,S)-alanyl]-5-aza-1-oxacyclooctane-4(S)-carboxylic acid A. Resolve 5-aza-1-oxacyclooctane-4-carboxylic acid as its d-camphorsulfonate. Dissolve in methanol and treat with thionyl chloride to obtain the methyl ester hydrochloride. Treat with pyruvic acid, triethylamine and dicyclohexylcarbodiimide in methylene chloride. Isolate methyl 5-pyruvoyl-5-aza-1-oxacyclooctane-4(S)-carboxylate by silica gel chromatography.

B. Combine 2.55 g of the above compound with -carbobenzyloxy-L-ornithine methyl ester (from 9.8 g of the hydrochloride salt) in 50 ml methanol, stir overnight and add 2.1 g NaCNBH$_3$. Stir overnight, concentrate and chromatograph on XAD-2 resin to obtain 5-[N-(1(S)-methoxycarbonyl-5-benzyloxycarbonylaminopentyl)-(R,S)-alanyl]-5-aza-1-oxacyclooctane-4(S)-carboxylic acid, methyl ester.

C. Dissolve the above material in 100 ml of methanol with 0.5 g 10% Pd/C and hydrogenate six hours at 3 atm. Filter, add 20 ml 1.0N NaOH, and stir two hours. Add 20 ml 1.0N HCl and remove the solvent. Chromatograph on XAD-2 resin to obtain the title compound.

EXAMPLE 47

1-[N-(1-Carboethoxy-3-phenylpropyl)-(S)-alanyl]hexahydrofuro[3,4-b]pyrrole-2(S)-carboxylic acid A. To a solution of ethyl hexahydrofuro[3,4-b]pyrrole-2-carboxylate in ethyl acetate add N-benzyloxycarbonyl-(S)-alanine, N-hydroxysuccinimide ester. Stir the reaction mixture at room temperature for 20 hours and concentrate it in vacuo. Place the residue on a column of silica gel (3000 g, 60–200 mesh) and elute with chloroform: ethyl acetate 10:1 to give 1-[N-benzyloxycarbonyl-(S)-alanyl]hexahydrofuro[3,4-b]pyrrole-2(R)-carboxylic acid, ethyl ester, and 1-[N-benzyloxycarbonyl(S)-alanyl]hexahydrofuro[3,4-b]pyrrole-2(S)-carboxylic acid, ethyl ester.

B. To a solution of 1 -[N-benzyloxycarbonyl- (S) -alanyl]hexahydrofuro[3,4 -b]pyrrole-2(S)-carboxylic acid, ethyl ester in methanol, add 2.5 N sodium hydroxide and stir the mixture at room temperature for 18 hours. Concentrate the mixture under nitrogen, dilute the residue with ice-water and then make the mixture acidic with concentrated hydrochloric acid. Extract the aqueous solution with ethyl acetate and dry the organic phase over magnesium sulfate. Concentrate the organic phase and place it on a column of silica gel. Elute with chloroform:glacial acetic acid 9:1 to give 1-[N-benzyloxycarbonyl-(S)-alanyl]hexahydrofuro[3,4-b ]pyrrole-2(S)-carboxylic acid.

C. Dissolve 1-[N-benzyloxycarbonyl-(S)-alanyl]hexhydrofuro[3,4-b]pyrrole-2(S)-carboxylic acid in methanol. Add 10% palladium-on-charcoal and hydrogenate the mixture at atmospheric pressure. Filter the mixture and concentrate in vacuo to give 1-[(S)-alanyl]hexahydrofuro[3,4-b]pyrrole-2(S)-carboxylic acid.

D. Dissolve 1-[(S)-alanyl]hexahydrofuro[3,4-b]pyrrole-2(S)-carboxylic acid (prepared in paragraph C of this example) in absolute methanol. Add 2-oxo-4-phenylbutyric acid, methyl ester and 3 Angstrom molecular sieve pellets, and stir the resulting mixture at room temperature for eighteen hours. Filter the reaction mixture and treat the filtrate with sodium cyanoborohydride at room temperature for two hours. Concentrate the mixture under nitrogen and dilute the oil with dilute hydrochloric acid and stir at room temperature for one hour. Absorb the aqueous solution on XAD-2 (Rohm & Hass Co.) resin. Elute the resin with water and then with methanol. Concentrate the methanol solution and place the residue on a column of silica gel and elute with chloroform:isopropanol: 7% ammonium hydroxide 1:1:1 (organic layer) to give 1-[N-(1-methoxycarbonyl-3-phenylpropyl)-(S)-alanyl]hexahydrofuro[3,4-b]pyrrole-2(S)carboxylic acid.

EXAMPLE 48

1-[N-(1-Carboxy-3-phenylpropyl)-(S)-alanyl]hexahydrofuro-[3,4-b]pyrrole2(S)-carboxylic acid To a solution of 1-[N-(1-carbomethoxy-3-phenylpropyl)-(S)-alanyl]hexahydrofuro[3,4-b]pyrrole-2(S)-carboxylic acid (prepared as described in Example 47) in methanol, add 2.5N sodium hydroxide. After three hours, concentrate the reaction mixture and absorb it on an XAD-2 resin column and elute with water and then with methanol. Concentrate the methanol eluant to give a residue and absorb this residue on a silica gel column and elute with chloroform: methanol: 14% ammonium hydroxide 1:1:1. Concentrate the desired eluant fractions to obtain the title compound.

EXAMPLE 49

1-[N-(1-Carboethoxy-3-phenylpropyl)-(S)-alanyl]-hexahydrofuro[3,4-b]pyrrole-2(S)-carboxylic acid React 1 -[(S)-alanyl]hexahydrofuro [3,4-b]pyrrole-2-(S)-carboxylic acid (prepared as described in Example 47) and ethyl phenyl-2-oxobutyrate with sodium cyanoborohydride as described in Example 47D (ethanol solvent) to obtain the title compound.

EXAMPLE 50

1-[N-(1-Carboethoxy-3-p-chlorophenylpropyl)-(S)-alanyl]-hexahydrofuro[3,4-b]pyrrole-2(S)-carboxylic acid Treat 1-[(S)-alanyl]hexahydrofuro[3,4-b]pyrrole-2-(S)-carboxylic acid (prepared as described in Example 47) and ethyl 4-(p-chlorophenyl)-2-oxobutyrate with sodium cyanoborohydride as described in Example 47D (ethanol solvent) to obtain the title compound.

EXAMPLE 51

1-[N-(1-Carboethoxy-3-phenylpropyl)-(S)-alanyl-]hexahydrothieno[3,4-b]pyrrole-2(S)-carboxylic acid Use ethyl hexahydrothieno [3,4-b]pyrrole-2-carboxylate in place of ethyl hexahydrofuro [3,4-b]pyrrole-2-carboxylate in Example 47A. Continue the sequence of reactions described in Example 47 through Example 47D to obtain the title compound. Example 47C is modified to employ HBr in acetic acid for liberation of the dipeptide.

EXAMPLE 52

1-[N-(1-Carboethoxy-3-phenylpropyl)-(S)-alanyl]-octahydropyrano[4,3-b]pyrrole-2(S)-carboxylic acid Use ethyl cis-octahydropyrano[4,3-b]pyrrole-2-carboxylate in place of ethyl hexahydrofuro [3,4-b]pyrrole-2-carboxylate in Example 47A through 47D to give the title compound.

EXAMPLE 53

1-[N-(1-Carboethoxy-3-phenylpropyl)-(S)-alanyl]-octahydrothiopyrano[3,4-b]pyrrole-2(S)-carboxylic acid Use ethyl octahydrothiopyrano [4,3-b]pyrrole-2-carboxylate in place of ethyl hexahydrofuro[3,4-b]pyrrole-2carboxylate in the procedure described in paragraphs A through D of Example 47 (modified as in Example 51) to give the title compound.

EXAMPLE 54

1-[N-(1-Carboethoxy-3-phenylpropyl)-(S)-alanyl]-octahydrofuro[3,4-b]pyridine-2(S)-carboxylic acid React ethyl octahydrofuro[3,4-b]pyridine-2-carboxylate with N-benzyloxycarbonyl- (S) -alanine, N-hydroxysuccinimide ester as described in Example 47A–D to isolate the title compound.

EXAMPLE 55

7-[N-(1-Carboethoxy-3-phenylpropyl)-(S)-alanyl]-2-thia-7-azaspiro[4.4 ]nonane-8(S)-carboxylic acid Treat 2-thia-7-azaspiro[4.4 ]nonane-8(S)-carboxylic acid ethyl ester in ethyl acetate with N-benzyloxycarbonyl-(S)-alanine, N-hydroxysuccinimide ester as described in Example 47A–D (modified as in Example 51]to isolate the title compound.

EXAMPLE 56

7-[N-(1-Carboxy-3-phenylpropyl)-(S)-alanyl]-2-thia-7-azaspiro[4.4]nonane-8(S)-carboxylic acid Hydrolzye 0.18 g of 7-[N-(1-carboethoxy-3-phenyl-propyl-(S)-alanyl]-2-thia-7-azaspiro[4.4]nonane-8(S)-carboxylic acid (prepared as described in Example 55) in 600 ml of methanol with 10 ml of 2.5N sodium hydroxide, concentrate the reaction mixture and absorb it on an XAD-2 resin column and elute with water and then with methanol. Concentrate the methanol eluant to give a residue and absorb this residue on a silica gel column (100 g, 60-200 mesh). Elute the column with chloroform: methanol: 14% ammonium hydroxide 1:1:1 and concentrate the desired eluant fractions to obtain the title compound.

EXAMPLE 57

7-[N-(1(S)-Carbomethoxy-3-methylthio)-(R,S)-alanyl]-2-thia-7-azaspiro[4.4]nonane-8(S)-carboxylic acid A. Couple 2-thia-7-azaspiro[4.4]nonane-8(S)-carboxylic acid, methyl ester with pyruvic acid using dicyclohexylcarbodiimide and triethylamine in dioxane to yield, after isolation and hydrolysis of the ester, 7-pyruvoyl-2-thia-7-azaspiro[4.4]nonane-8(S)-carboxylic acid.

B. Condense 7-pyruvoyl-2-thia-7-azaspiro[4.4]nonane-8(S)-carboxylic acid and (S)-methionine, methyl ester with sodium cyanoborohydride in methanol at pH 7 for three days at room temperature followed by chromatography on a XAD-2 resin column, using methanol as eluant, to obtain the title compound.

EXAMPLE 58

7-[N-(1-Carboethoxy-3-phenylpropyl)glycyl]-2-thia-7-azaspiro[4.4]nonane-8(S)-carboxylic acid Couple 2-thia-7-azaspiro[4.4]nonane-8(S)-carboxylic acid, ethyl ester with N-benzyloxycarbonylglycine, N-hydroxysuccinimide ester as described in Example 23C-F to yield the title compound.

EXAMPLE 59

7-[N-(1-Carboxy-3-phenylpropyl)glycyl]-2-thia-7-azaspiro[4.4]nonane-8(S)-carboxylic acid As described in Example 48, hydrolyse 7-[N-(1-carboethoxy-3-phenylpropyl)glycyl]-2-thia-7-azaspiro[4.4-]nonane-8(S)-carboxylic acid (prepared as described in Example 58 with sodium hydroxide to give the title compound.

EXAMPLE 60

1-[N-(1-Carboethoxy-3-phenylpropyl-(S)-alanyl]-7-oxa-1-azaspiro[4.4]nonane-2(S)-carboxylic acid Use 7-oxa-1-azaspiro[4.4]nonane-2-carboxylic acid, ethyl ester in place of hexahydrofuro[3,4-b]pyrrole-2-carboxylic acid, ethyl ester in Example 47A through 47D to obtain the title compound.

EXAMPLE 61

2-[N-(1-Carboethoxy-3-phenylpropyl)-(S)-alanyl]-8-thia-2-azaspiro[4.5]decane-3(S)-carboxylic acid As described in Example 47A through 47D (modified as in Example 51), substitute 8-thia-2-azaspiro[4.5]decane-3-carboxylic acid, ethyl ester for hexahydrofuro [3,4 -b]pyrrole-2-carboxylic acid, ethyl ester to obtain the title compound.

EXAMPLE 62

7-[N-(1-Carboethoxy-3-phenylpropyl)-(S)-alanyl]-2-oxa-7-azaspiro[4.5]decane-8(S)-carboxylic acid Combine ethyl 2-oxa-7-azaspiro[4.5]decane-8-carboxylate and N-benzyloxycarbonyl-(S)-alanine, N-hydroxysuccinimide ester by the procedure described in Example 47A–D to obtain the title compound.

EXAMPLE 63

N-(1 (R)-Ethoxycarbonyl-2-benzylthioethyl)-(R,S)-alanyl-(S)proline hydrochloride Mix 8.28 g of S-benzyl-L-cysteine ethyl ester hydrochloride with NaHCO$_3$ solution until basic. Extract with dichloromethane, dry with MgSO$_4$, and concentrate to dryness at room temperature. Dissolve the residue in 80 ml of tetrahydrofuran containing 2.1 g of pyruvoyl-L-proline and 4 g of 5 Angstrom molecular sieves. Stir for 2 days and then add, dropwise over 4 hours, a solution of sodium cyanoborohydride in 20 ml of ethanol. Stir for 18 hours, filter, and concentrate the filtrate to dryness. Partition the residue between water and dichloromethane. Absorb the aqueous phase on a sulfonic acid ion exchange resin and elute with 4% pyridine in water. Concentrate to dryness. Dissolve the residue in a mixture of 5 ml of methanol and 1500 ml ether. Acidify this solution with 3.5M HCl in ether and filter the resulting precipitate to obtain 2.5 g of the title compound having a melting point of 90°–100° C. and $a_D^{26} = -73.4°$ (1%, H$_2$O).

EXAMPLE 64

N-(1(S)-Ethoxycarbonyl-2-benzyloxyethyl)-(R,S)-alanyl-(S)-proline hydrochloride

Following the procedure of Example 63, react 5 g of O-benzyl-L-serine ethyl ester hydrochloride with 1.26 g of pyruvoyl-L-proline to yield 1.6 g of the title compound having a melting point of 90°–100° and $a_D^{26} = -71.3°$ (1%, H$_2$O).

EXAMPLE 65

1-[N-(1(S)-Carboethoxy-3-phenylpropyl)-(S)-alanyl-octrahydroindole-2(S)-carboxylic acid Following the procedure of Example 1, but modifying step E to use ethanol as reaction solvent, prepare 1-[N-(1(R,S)carboethoxy-3-phenylpropyl)-(S)-alanyl-octahydroindole-2(S)-carboxylic acid. Chromatograph this material on an RP-8 reversed-phase column using acetonitrile: 0.2N NH$_4$OAc 40:60 (pH 8.6) as eluent to obtain the title compound as a solid $[\alpha]_D^{26} = -45.3°$ (ethanol).

Similarly, prepare the following compounds:
1-[N-(1-carboethoxy-3-phenylpropyl)-(S)-alanyl]octahydroindole-2(S)-carboxylic acid;
1-[N-(1 -carboethoxy-2-phenylethyl)-(S)-alanyl]octahydroindole-2(S)-carboxylic acid;
1-[N-(1 -carboxy-2-phenylethyl)-(S)-alanyl]octahydroindole-2(S)-carboxylic acid;
1-[N-(1 -carboethoxy-2-phenylthioethyl)-(S)-alanyl]octahydroindole-2(S)-carboxylic acid;
1-[N-(1-carbomethoxy-3-phenylpropyl)-(S)-alanyl]-decahydrocyclohepta[b]pyrrole-2(S)-carboxylic acid;

7-[N-(1-carboethoxy-3-phenylpropyl)-(S)-alanyl]-1-thia-7-azaspiro[4.4]nonane-8(S)-carboxylic acid;

1-[N-(1-carbomethoxy-3-phenylpropyl)-(S)-lysyl]octahydroindole-2(S)-carboxylic acid;

1-[N-(1-carboethoxy-2-benyloxyethyl)-(S)-alanyl]octahydroindole-2(S)-carboxylic acid;

N-(1-carboethoxy-2-benzylthioethyl)-(S)-alanyl]octahydroindole-2(S)-carboxylic acid;

1-[N-(1-carboethoxyethyl)-(S)-alanyl]octahydroindole-2(S)-carboxylic acid;

1-[N-(1-carboethoxy-2-cyclohexylethyl)-(S)-alanyl]octahydroindole-2(S)-carboxylic acid;

1-[N-(1-carboethoxy-5-methylhexyl)-(S)-alanyl]octahydroindole-2(S)-carboxylic acid;

1-[N-(1-carbomethoxy-3-phenylpropyl)-(S)-alanyl]octahydrocyclopenta[b]pyrrole-2(S)-carboxylic acid;

1-[N-(1-carboethoxy-3-phenylpropyl)-(S)-alanyl]octahydrocyclopenta[c]pyrrole-2(S)-carboxylic acid;

1-[N-(1-carboxy-3-phenylpropyl)-(S)-alanyl]octahydrocyclopenta[c]pyrrole-2(S)-carboxylic acid;

1-[N-(1-Carbomethoxy-3-phenylpropyl)-(S)-alanyl]-decahydroquinoline-2(S)-carboxylic acid;

1-[N-(1-carboxy-3-phenylpropyl)glycyl]decahydroquinoline-2(S)-carboxylic acid;

1-[N-(1-carboethoxy-3-p-chlorophenylpropyl)-(S)-alanyl]decahydroquinoline-2(S)-carboxylic acid;

1-[N-(1-carboxy-2-phenylethyl)-(S)-alanyl]octahydroisoindole-1(S)-carboxylic acid;

4-[N-(1-carboethoxy-3-phenyl propyl)-(S)-alanyl]octahydrofuro[3,2-b]pyrrole-5(S)-carboxylic acid;

1-[N-(1-carboethoxy-3-phenylpropyl)-(S)-alanyl]octahydropyrano[3,2-b]pyrrole-2(S)-carboxylic acid;

4-[N-(1-carboethoxy-3-phenylpropyl)-(S)-alanyl]octahydrothieno[3,2-b]pyrrole-5(S)-carboxylic acid;

5-[N-(1-carboethoxy-3-phenylpropyl)-(S)-alanyl]octahydrofuro[2,3-c]pyrrole-4(S)-carboxylic acid;

5-[N-(1-carboethoxy-3-phenylpropyl)-(S)-alanyl]octahydrothieno[2,3-c]pyrrole-4(S)-carboxylic acid;

4-[N-(1-carboethoxy-3-phenylpropyl)-(S)-alanyl]octahydrofuro[3,2-b]pyridine-5(S)-carboxylic acid;

5-[N-(1-carboethoxy-3-phenylpropyl)-(S)-alanyl]-decahydropyrano[3,2-b]pyridine-6(S)-carboxylic acid;

4-[N-(1-carboethoxy-3-phenylpropyl)-(S)-alanyl]octahydrothieno[3,2-b]pyridine-5(S)-carboxylic acid;

5-[N-(1-carboethoxy-3-phenylpropyl)-(S)-alanyl]-decahydrothiopyrano[3,2-b]pyridine-6(S)-carboxylic acid;

6-[N-(1-carboethoxy-3-phenylpropyl)-(S)-alanyl]octahydrofuro[2,3-c]pyridine-5(S)-carboxylic acid;

7-[N-(1-carboethoxy-3-phenylpropyl)-(S)-alanyl]-decahydropyrano[2,3-c]pyridine-6(S)-carboxylic acid;

6-[N-(1-carboethoxy-3-phenylpropyl)-(S)-alanyl]octahydrothieno[2,3-c]pyridine-5(S)-carboxylic acid;

7-[N-(1-carboethoxy-3-phenylpropyl)-(S)-alanyl]-decahydrothiopyrano[2,3-c]pyridine-6(S)-carboxylic acid; 5-[N-(1-carboxy-3-phenylpropyl)-(S)-alanyl]-2,2-dimethyloctahydro-1,3-dioxolo[4,5-c]pyrrole-4(S)-carboxylic acid;

6-[N-(1-carboxy-3-phenylpropyl)-(S)-alanyl]octahydro-1,4-dioxino[2,3-c]pyrrolo-5(S)-carboxylic acid;

5-[N-(1-carboxy-3-phenylpropyl)-(S)-alanyl]octahydro-1,3-dithiolo[4,5-c]pyrrole-4(S)-carboxylic acid;

6-[N-(1-carboxy-3-phenylpropyl)-(S)-alanyl]octahydro-1,4-dithiino[2,3-c]pyrrole-5(S)-carboxylic acid;

5-[N-(1-carboxy-3-phenylpropyl)-(S)-alanyl]-2,2dimethyloctahydro-1,3-dioxolo[4,5-c]pyridine-6(S)-carboxylic acid;

6-[N-(1-carboxy-3-phenylpropyl)-(S)-alanyl]decahydro-1,4-dioxino[4,5-c]pyridine-7(S)-carboxylic acid;

5-[N-(1-carboxy-3-phenylpropyl)-(S)-alanyl]octahydro-1,3-dithiolo[4,5-c]pyridine-6(S)-carboxylic acid;

6-[N-(1-carboxy-3-phenylpropyl)-(S)-alanyl]decahydro-1,4-dithiino[2,3-c]pyridine-7(S)-carboxylic acid;

5-[N-(1-carboxy-3-phenylpropyl)-(S)-alanyl]octahydro-1,3-dioxolo[4,5-c]pyridine-4(S)-carboxylic acid;

6-[N-(1-carboxy-3-phenylpropyl)-(S)-alanyl]decahydro-1,4-dioxino[2,3-c]pyridine-5(S)-carboxylic acid;

5-[N-(1-carboxy-3-phenylpropyl)-(S)-alanyl]octahydro-1,3-dithiolo [4,5-c]pyridine-4(S)-carboxylic acid;

6-[N-(1-carboxy-3-phenylpropyl)-(S)-alanyl]decahydro-1,4-dithiino[2,3-c]pyridine-5(S)-carboxylic acid;

7-[N-(1-carboethoxy-3-p-chlorophenylpropyl)-(S)-alanyl]-1,4-dithia-7-azaspiro[4.4 ]nonane-8(S)-carboxylic acid;

7-[N-(1-carboxy-3-p-chlorophenylpropyl)-(S)-alanyl]-1,4-dithia-7-azaspiro[4.4]nonane-8(S)-carboxylic acid;

7-[N-(1-carboxy-2-phenoxyethyl)-(S)-alanyl]-1,4-dithia-7-azaspiro[4.4]nonane-8(S)-carboxylic acid;

7-[N-(1-carbomethoxy-3-methylthiopropyl)-(R,S)-alanyl]-1,4-dithia-7-azaspiro[4.4]nonane-8(S)-carboxylic acid;

7-[N-(1-carboxy-3-methylthiopropyl)-(R,S)-alanyl]-1,4-dithia-7-azaspiro[4.4]nonane-8(S)-carboxylic acid;

7-{N-[1-carboethoxy-2-(3-indolyl)ethyl]-(R,S)-alanyl}-1,4-dithia-7-azaspiro[4.4]nonane-8(S)-carboxylic acid;

7-{N-[1-carboxy-2-(3-indolyl)ethyl]-(R,S)-alanyl}-1,4-dithia-7-azaspiro[4.4]nonane-8(S)-carboxylic acid;

7-{N-[1-carboethoxy-2-(1H-imidazol-4-yl)ethyl]-(R,S)-alanyl}-1,4-dithia-7-azaspiro[4.4]nonane-8(S)-carboxylic acid;

7-[N-(1-carbomethoxy-3-phenylpropyl)glycyl]-1,4-dithia-7-azaspiro[4.4 ]nonane-8(S)-carboxylic acid;

7-[N-(1-carboethoxy-3-phenylpropyl)-(S)-alanyl]-1,4-dioxa-7-azaspiro[4.4]nonane-8(S)carboxylic acid;

2-[N-(1-carboethoxy-3-phenylpropyl)-(S)-alanyl]-6,10-dioxa-2-azaspiro[4.5]decane-3(S)-carboxylic acid;

2-[N-(1-carboethoxy-3-phenylpropyl)-(S)-alanyl]-6,10-dithia-2-azaspiro [4.5 ]decane-3(S)-carboxylic acid;

7-[N-(1-carboethoxy-3-phenylpropyl)-(S)-alanyl]-1,4-dioxa-7-azaspiro[4.4 ]nonane-6(S)-carboxylic acid;

2-[N-(1-carboethoxy-3-phenylpropyl)-(S)-alanyl]-6,10-dioxa-2-azaspiro[4.5 ]decane-1(S)-carboxylic acid;

7-[N-(1-carboethoxy-3-phenylpropyl)-(S)-alanyl]-1,4-dithia-7-azaspiro[4.4]nonane-6(S)-carboxylic acid:

2-[N-(1-carboethoxy-3-phenylpropyl)-(S)-alanyl]-6,10-dithia-2-azaspiro[4.5]decane-1(S)-carboxylic acid;

7-[N-(1-carboethoxy-3-phenylpropyl)-(S)-alanyl]-1,4-dioxa-7-azaspiro [4.5]decane-8(S)-carboxylic acid;

7-[N-(1-carboethoxy-3-phenylpropyl)-(S)-alanyl]-1,4-dithia-7-azaspiro[4.5]decane-8(S)-carboxylic acid;

8-[N-(1-carboethoxy-3-phenylpropyl)-(S)-alanyl]-1,5-dithia-8-azaspiro[5.5]undecane-9(S)-carboxylic acid;

8-[N-(1-carboethoxy-3-phenylpropyl)-(S)-alanyl]-1,4-dioxa-8-azaspiro[4.5]decane-7(S)-carboxylic acid;

9-[N-(1-carboethoxy-3-phenylpropyl)-(S)-alanyl]-1,5-dioxa-9-azaspiro[5.5 ]undecane-8(S)-carboxylic acid;

8-[N-(1-carboethoxy-3-phenylpropyl)-(S)-alanyl]-1,4-dithia-8-azaspiro[4.5]decane-7(S)-carboxylic acid;

9-[N-(1-carboethoxy-3-phenylpropyl)-(S)-alanyl]-1,5-dithia-9-azaspiro[5.5]undecane-8(S)-carboxylic acid;

1-[1-carboethoxy-3-phenylpropyl)-(S)-alanyl]-4,4-dimethoxy-(S)-proline;
1-[N-(1-carboethoxy-3-phenylpropyl)-(S)-alanyl]-5,5-dimethoxy-(S)-pipecolic acid;
1-[N-(1-carboethoxy-3-phenylpropyl)-(S)-alanyl]-3,3-dimethoxy-(S)-proline;
1-[N-(1-carboethoxy-3-phenylpropyl)-(S)-alanyl]-4,4-dimethoxy-(S)-pipecolic acid;
1-[N-(1-carboethoxy-3-phenylpropyl)-(S)-alanyl]-4,4-di(ethylthio)-(S)-proline;
1-[N-(1-carboethoxy-3-phenylpropyl)-(S)-alanyl]-3,3-di(ethylthio)-(S)-proline;
1-[N-(1-carboethoxy-3-phenylpropyl)-(S)-alanyl]-5,5-di(ethylthio)-(S)-pipecolic acid;
1-[N-(1-carboethoxy-3-phenylpropyl)-(S)-alanyl]-4,4-di(ethylthio)-(S)-pipecolic acid;
1-[N-(1-carboethoxy-3-phenylpropyl)-(S)-alanyl]-1-azaspiro[4.5]decane-2(S)-carboxylic acid;
2-[N-(1-carboethoxy-3-phenylpropyl]-2-azaspiro[04.5]-decane-3(S)-carboxylic acid;
2-[N-(1-carboethoxy-3-phenylpropyl)-(S)-alanyl]-2-azaspiro[4.5]decane-7(S)-carboxylic acid;
2-[N-(1-carboethoxy-3-phenylpropyl)-(S)-alanyl]-1-azaspiro[5.5]undecane-2(S)-carboxylic acid;
2-[N-(1-carboethoxy-3-phenylpropyl)-(S)-alanyl]-7-azaspiro[4.5]decane-8(S)-carboxylic acid;
2-[N-(1-carboethoxy-3-phenylpropyl)- (S)-alanyl]-2-azaspiro[5.5]undecane-3(S)-carboxylic acid;
8-[N-(1-carboethoxy-3-phenylpropyl)-(S)-alanyl]-8-azaspiro[4.5]decane-7(S)-carboxylic acid;
3-[N-(1-carboethoxy-3-phenylpropyl)-(S)-alanyl]-3-azaspiro[5.5]undecane-2(S)-carboxylic acid;
7-[N-(1-carboethoxy-3-phenylpropyl)-(S)-alanyl]-1-oxa-7-azaspiro[4.4]nonane-8(S)-carboxylic acid;
7-[N-(1-carboethoxy-3-phenylpropyl)-(S)-alanyl]-1-oxa-7-azaspiro[4.4]nonane-6(S)-carboxylic acid;
7-[N-(1-carboethoxy-3-phenylpropyl)-(S)-alanyl]-1-oxa-7-azaspiro[4.5]decane-8(S)-carboxylic acid;
8-[N-(1-carboethoxy-3-phenylpropyl)-(S)-alanyl]-1-oxa-8-azaspiro[5.5]undecane-9(S)-carboxylic acid;
8-[N-(1-carboethoxy-3-phenylpropyl)-(S)-alanyl]-1-oxa-8-azaspiro[4.5]decane-7(S)-carboxylic acid;
9-[N-(1-carboethoxy-3-phenylpropyl)-(S)-alanyl]-1-oxa-9-azaspiro[5.5]undecane-8(S)-carboxylic acid;
1-[N-(1-carboethoxy-3-phenylpropyl)-(S)-alanyl]-4(R,S)-(1,3-dioxolan-2-yl)-(S)-proline;
1-[N-(1-carboethoxy-3-phenylpropyl)-(S)-alanyl]-4(R,S)-(1,3-dioxan-2-yl)-(S)-proline;
1-[N-(1-carboethoxy-3-phenylpropyl)-(S)-alanyl]-4(R,S)-(1,3-dithiolan-2-yl)-(S)-proline;
1-[N-(1-carboethoxy-3-phenylpropyl)-(S)-alanyl]-4(RS)-dimethoxymethyl-(S)-proline;
1-[N-(1-carboethoxy-3-phenylpropyl)-(S)-alanyl]-4(R,S)-di(ethylthio)methyl-(S)-proline;
1-[N-(1-carboethoxy-3-phenylpropyl)-(S)-alanyl]-4(R,S)-(2-tetrahydrofuryl)-(S)-proline;
1-[N-(1-carboethoxy-3-phenylpropyl)-(S) alanyl]-4(R,S)-(2-tetrahydropyranyl)-(S)-proline;
1-[N-( t-carboxy-3-phenylpropyl)-(S)-alanyl]-4(R,S)-(1,3-dioxolan-2-yl)-(S)-proline;
1-[N-(1-carboxy-3-phenylpropyl)glycyl]-4(R,S)-(1,3-dioxalan-2-yl)-(S)-proline;
1-[N-(1-carboxy-3-phenylpropyl)-(S)-alanyl-]4(R,S)-(1,3-dithiolan-2-yl)-(S)-proline;
1-[N-(1-carboxy-3-phenylpropyl)glycyl[-4(R,S)-(1,3-dithiolan-2-yl)-(S)-proline;
1-[N-(1-carboxy-3-phenylpropyl)-(S)-alanyl]-4(R,S)-dimethoxymethyl-(S)-proline;
1-[N-(1-carboxy-3-phenylpropyl)-(S)-alanyl]-4-(R,S)-di(ethylthio)methyl-(S)-proline;
1-[N-(1-carboxy-3-phenylpropyl)-(S)-alanyl-]4(R,S)-(2-tetrahydrofuryl)-(S)-proline;
1-[N-(1-carboxy-3-phenylpropyl)-(S)-alanyl]-4(R,S)-(2-tetrahydropyranyl)-(S)-proline;
1-[N-(1-carboxy-3-phenylpropyl)glycyl]-4(R,S)-(2- tetrahydropyranyl)-(S)-proline;
N-[N-(1-carboethoxy-3-phenylpropyl)-(S)-alanyl]-N-(2,2-diethoxy)ethyl-(S)-alanine;
N-[N-(1-carboethoxy-3-phenylpropyl)-(S)-alanyl]-N-(1,3-dioxolan-2-yl)methyl-(S)-alanine;
N-[N-(1-carboethoxy-3-phenylpropyl)-(S)-alanyl]-N-(1,3-dioxan-2-yl)methyl-(S)-alanine;
N-[N-(1-carboethoxy-3-phenylpropyl)-(S)-alanyl]-N-(1,3-dithiolan-2-yl)methyl-(S)-alanine;
N-[N-(1-carboethoxy-3-phenylpropyl)-(S)-alanyl]-N-(1,3-dithian-2-yl)methyl- (S)-alanine;
N-[N-(1-carboethoxy-3-phenylpropyl)-(S)-alanyl]-N-(2-tetrahydrofuryl)methyl-(S)-alanine;
N-[N-(1-carboethoxy-3-phenylpropyl)-(S)-alanyl]-N-(2-tetrahydropyranyl)methyl-(S)-alanine;
N-[N-(1-carboethoxy-3-phenylpropyl)-(S)-alanyl]-N-(2-tetrahydrothienyl)methyl-(S)-alanine; N-[N-[carboethoxy-3-phenylpropyl)-(S)-alanyl]-N-cyclohexyl-(S)-alanine;
N-[N-(1-carboethoxy-3-phenylpropyl)-(S)-alanyl]-N-cyclopentyl-(S)-alanine;
N-[N-(1-carboethoxy-3-phenylpropyl)-(S)-alanyl]-3-(2-methyl-1,3-dioxolan-2-yl)-(S)-alanine;
N-[N-(1-carboethoxy-3-phenylpropyl)-(S)-alanyl]-3(2-methyl-1,3-dithiolan-2-yl)-(S)-alanine;
N-[N-(1-carboethoxy-3-phenylpropyl)-(S)-alanyl]-3-(2-methyl-1,3-dioxan-2-yl)-(S)-alanine;
N-[N-(1-carboethoxy-3-phenylpropyl)-(S)-alanyl]-3-(2-methyl-1,3-dithian-2-yl)-(S)-alanine;
N-[N-(1-carboethoxy-3-phenylpropyl)-(S)-alanyl]-3-(2-methyl-2-tetrahydrofuryl)-(S)-alanine;
N-[N-(1-carboethoxy-3-phenylpropyl)-(S)-alanyl]-3-(2-methyl-2-tetrahydropyranyl)-(S)-alanine;
N-[N-(1-carboethoxy-3-phenylpropyl)-(S)-alanyl]-3-(2-methyl-2-tetrahydrothienyl)-(S)-alanine;
N-[N-(1-carboethoxy-3-phenylpropyl)-(S)-alanyl]-3-(2-methyl-2-tetrahydrothiopyranyl)-(S)-alanine;
1-[N-(1-carboxy-3-phenylpropyl)-(S)-alanyl]-azacyclononane-2(S)-carboxylic acid;
1-[N-(1-ethoxycarbonyl-3-phenylpropyl)-(S)-alanyl]-azacyclodecane-2(S)-carboxylic acid;
1-[N-(1-carboxy-3-phenylpropyl)-(S)-alanyl]-azacyclodecane-2(S)-carboxylic acid;
1-[N-α-(1-methoxycarbonyl-3-phenylpropyl)-(S)-lysyl]-azacyclooctane-2(S)-carboxylic acid;
1-[N-α-(1-carboxy-3-phenylpropyl)-(S)-lysyl]-azacyclononane-2(S)-carboxylic acid;
1-[N-(1(S)-carboxy-5-aminopentyl)alanyl]-azacyclononane-2(S)-carboxylic acid;
4-[N-(1-ethoxycarbonyl-3-phenylpropyl)-(S)-alanyl]-4-aza-1-oxacyclooctane-5(S)-carboxylic acid;
4-[N-(1-ethoxycarbonyl-3-phenylpropyl)-(S)-alanyl]-4-aza-1-thiacyclooctane-3(S)-carboxylic acid;
5-[N-(1-carboxy-3-phenylpropyl)-(S)-alanyl]-5-aza-1-oxacyclononane-6(S)-carboxylic acid;
5-[N-(1-ethoxycarbonyl-3-phenylpropyl)-(S)-alanyl]-5-aza-1-oxacyclononane-4(S)-carboxylic acid; 4-[N-ethoxycarbonyl-3-phenylpropyl)-(S)-alanyl]-4-aza-1-thiacyclononane-3(S)-carboxylic acid;
4-[N-(1-carboxy-3-phenylpropyl)-(S)-alanyl]-4-aza-1-oxacyclodecane-5(S)-carboxylic acid;

5-[N-(1-ethoxycarbonyl-3-phenylpropyl)-(S)-alanyl]-5-aza-1-oxacyclodecane-6(S)-carboxylic acid;
6-[N-(1-methoxycarbonyl-3-phenylpropyl)-(S)-alanyl]-6-aza-1-thiacyclodecane-5(S)-carboxylic acid;
5-[N-(1-ethoxycarbonyl-3-phenylpropyl)-(S)-alanyl]-5-aza-1-oxacyclodecane-4(S)-carboxylic acid;
4-[N-(1-ethoxycarbonyl-3-phenylpropyl)-(S)-alanyl]-4-aza-1-oxacyclodecane-3(S)-carboxylic acid;
1-[N-(1-carbomethoxy-3-phenylpropyl)-(S)-alanyl]hexahydrofuro[3,4-b]pyrrole-2(S)-carboxylic acid;
1-[N-(1-carboethoxy-2-phenylethyl)-(S)-alanyl]hexahydrofuro[3,4-b]-pyrrole-2(S)-carboxylic acid;
1-[N-(1-carboxy-2-phenylethyl)-(S)-alanyl]hexahydrofuro [3,4-b]pyrrole-2(S)-carboxylic acid;
5-[N-(1-carboethoxy-3-phenylpropyl)-(S)-alanyl]hexahydrofuro[3,4-c]pyrrole-4(S)-carboxylic acid;
1-[N-(1-carboethoxy-3-phenylpropyl)-(S)-alanyl]hexahydrothieno[3,4-b]pyrrole-2(S)-carboxylic acid;
5-[N-(1-carboethoxy-3-phenylpropyl)-(S)-alanyl]hexahydrothieno[3,4-c]pyrrole-4(S)-carboxylic acid;
1-[N-(1-carboethoxy-3-phenylpropyl)-(S)-alanyl]octahydropyrano[3,4-b]pyrrole-2(S)-carboxylic acid;
1-[N-(1-carboethoxy-3-phenylpropyl)-(S)-alanyl]octahydropyrano[3,4-c]pyrrole-2(S)-carboxylic acid;
2-[N-(1-carboethoxy-3-phenylpropyl)-(S)-alanyl]octahydropyrano[3,4-c]pyrrole-3(S)-carboxylic acid;
2-[N-(1-carboethoxy-3-phenylpropyl)-(S)-alanyl]octahydropyrano[3,4-c]pyrrole-1-(S)-carboxylic acid;
1-[N-(1-carboethoxy-3-phenylpropyl)-(S)-alanyl]octahydrothiopyrano[4,3-b]pyrrole-2(S)-carboxylic acid;
1-[N-(1-carboethoxy-3-phenylpropyl)-(S)-alanyl]octahydrothiopyrano[3,4-b]pyrrole-2(S)-carboxylic acid;
2-[N-(1-carboethoxy-3-phenylpropyl)-(S)-alanyl]octahydrothiopyrano[3,4-c]pyrrole-1(S)-carboxylic acid;
2-[N-(1-carboethoxy-3-phenylpropyl)-(S)-alanyl]octahydrothiopyrano[3,4-c]pyrrole-3(S)-carboxylic acid;
1-[N-(1-carboethoxy-3-phenylpropyl)-(S)-alanyl]octahydrofuro[3,4-b]pyridine-2(S)-carboxylic acid;
5-[N-(1-carboethoxy-3-phenylpropyl)-(S)-alanyl]octahydrofuro[3,4-c]pyridine-6(S)-carboxylic acid;
5-[N-(1-carboethoxy-3-phenylpropyl)-(S)-alanyl]octahydrofuro[3,4-c]pyridine-4(S)-carboxylic acid;
1-[N-(1-carboethoxy-3-phenylpropyl)-(S)-alanyl]octahydrothieno[3,4-b]pyridine-2(S)-carboxylic acid;
5-[N-(1-carboethoxy-3-phenylpropyl)-(S)-alanyl]octahydrothieno[3,4-c]pyridine-6(S)-carboxylic acid;
5-[N-(1-carboethoxy-3-phenylpropyl)-(S)-alanyl]octahydrothieno[3,4-c]pyridine-4(S)-carboxyl i c acid;
1-[N-(1-carboethoxy-3-phenylpropyl)-(S)-alanyl]octahydropyrano[3,4-b]pyridine-2(S)-carboxylic acid;
1-[N-(1-carboethoxy-3-phenylpropyl)-(S)-alanyl]octahydropyrano[4,3-b]pyridine-2(S)-carboxylic acid;
7-[N-(1-carboethoxy-3-phenylpropyl)-(S)-alanyl]octahydropyrano[3,4-c]pyridine-6(S)-carboxylic acid;
6-[N-(1-carboethoxy-3-phenylpropyl)-(S)-alanyl]octahydropyrano[4,3-c]pyridine-7(S)-carboxylic acid;
6-[N-(1-carboethoxy-3-phenylpropyl)-(S)-alanyl]octahydropyrano[4,3-c]pyridine-5(S)-carboxylic acid;
7-[N-(1-carboethoxy-3-phenylpropyl)-(S)-alanyl]octahydropyrano[3,4-c]pyridine-8(S)-carboxylic acid;
1-[N-(1-carboethoxy-3-phenylpropyl)-(S)-alanyl]octahydrothiopyrano[3,4-b]pyridine-2(S)-carboxylic acid;
1-[N-(1-carboethoxy-3-phenylpropyl)-(S)-alanyl]octahydrothiopyrano[4,3-b]pyridine-2(S)-carboxylic acid;
7-[N-(1-carboethoxy-3-phenylpropyl)-(S)-alanyl]octahydrothiopyrano[3,4-c]pyridine-6(S)-carboxylic acid;
6-[N-(1-carboethoxy-3-phenylpropyl)-(S)-alanyl]octahydrothiopyrano[4,3-c]pyridine-7(S)-carboxylic acid;
6-[N-(1-carboethoxy-3-phenylpropyl)-(S)-alanyl]octahydrothiopyrano[4,3-c]pyridine-5(S)-carboxylic acid;
7-[N-(1-carboethoxy-3-phenylpropyl)-(S)-alanyl]octahydrothiopyrano[3,4-c]pyridine-8(S)-carboxylic acid;
5-[N-(1-carboxy-3-phenylpropyl)-(S)-alanyl]octahydrofuro[3,4-c]pyridine-6(S)carboxylic acid;
1-[N-(1-carboxy-3-phenylpropyl)-(S)-alanyl]octahydrothieno[3,4-b]pyridine-2(S)-carboxylic acid;
5-[N-(1-carboxy-3-phenylpropyl)-(S)-alanyl]octahydrothieno[3,4-c]pyridine-4(S)-carboxylic acid;
1-[N-(1-carboxy-3-phenylpropyl)-(S)-alanyl]octahydropyrano[3,4-b]pyridine-2(S)-carboxylic acid;
7-[N-(1-carboxy-3-phenylpropyl)-(S)-alanyl]octahydropyrano[3,4-c]pyridine-6(S)-carboxylic acid;
7-[N-(1-carboethoxy-3-phenylpropyl)-(S)-alanyl]-2-oxa-7-azaspiro[4.4]nonane-8(S)-carboxylic acid;
1-[N-(1-carbomethoxy-3-phenylpropyl)-(S)-alanyl]-7-oxa-1-azaspiro[4.4]nonane-2(S)-carboxylic acid;
7-[N-(1-carboethoxy-3-phenylpropyl)-(S)-alanyl]-2-oxa-7-azaspiro[4.4]nonane-6(S)-carboxylic acid;
7-[N-(1-carbomethoxy-3-phenylpropyl)-(S)-alanyl]-2-thia-7-azaspiro[4.4]nonane-8(S)-carboxylic acid;
1-[N-(1-carboethoxy-3-phenylpropyl)-(S)-alanyl]-7-thia-1-azaspiro[4.4]nonane-2(S)-carboxylic acid;
7-[N-(1-carboethoxy-3-phenylpropyl)-(S)-alanyl]-2-thia-7-azaspiro[4.4]nonane-6(S)-carboxylic acid;
2-[N-(1-carboethoxy-3-phenylpropyl)-(S)-alanyl]-7-oxa-2-azaspiro[4.5]decane-3(S)-carboxylic acid;
2-[N-(1-carboethoxy-3-phenylpropyl)-(S)-alanyl]-8-oxa-2-azaspiro[4.5]decane-3(S)-carboxylic acid;
1-[N-(1-carboethoxy-3-phenylpropyl)-(S)-alanyl]-7-oxa-1-azaspiro[4.5]decane-2(S)-carboxylic acid;
1-[N-(1-carboethoxy-3-phenylpropyl)-(S)-alanyl]-8-oxa-1-azaspiro[4.5]decane-2(S)-carboxylic acid;
2-[N-(1-carboethoxy-3-phenylpropyl)-(S)-alanyl]-7-oxa-2-azaspiro[4.5]decane-1(S)-carboxylic acid;
2-[N-(1-carboethoxy-3-phenylpropyl)-(S)-alanyl]-8-oxa-2-azaspiro[4.5]decane-1(S)-carboxylic acid;
2-[N-(1-carboethoxy-3-phenylpropyl)-(S)-alanyl]-7-thia-2-azaspiro[4.5]decane-3(S)-carboxylic acid;
2-[N-(1-carbomethoxy-3-phenylpropyl)-(S)-alanyl]-8-thia-2-azaspiro[4.5]decane-3(S)-carboxylic acid;
1-[N-(1-carboethoxy-3-phenylpropyl)-(S)-alanyl]-7-thia-1-azaspiro[4.5]decane-2(S)-carboxylic acid;
1-[N-(1-carboethoxy-3-phenylpropyl)-(S)-alanyl]-8-thia-1-azaspiro[4.5]decane-2(S)-carboxylic acid;
2-[N-(1-carboethoxy-3-phenylpropyl)-(S)-alanyl]-7-thia-2-azaspiro[4.5]decane-1(S)-carboxylic acid;
2-[N-(1-carbomethoxy-3-phenylpropyl)-(S)-alanyl]-8-thia-2-azaspiro[4.5]decane-1(S)-carboxylic acid;
6-[N-(1-carboethoxy-3-phenylpropyl)-(S)-alanyl]-2-oxa-6-azaspiro[4.5]decane-7(S)-carboxylic acid;
7-[N-(1-carbomethoxy-3-phenylpropyl)-(S)-alanyl]-2-oxa-7-azaspiro[4.5]decane-8(S)-carboxylic acid;
8-[N-(1-carboethoxy-3-phenylpropyl)-(S)-alanyl]-2-oxa-8-azaspiro[4.5 ]decane-7(S)-carboxylic acid;

7-[N-(1-carboethoxy-3-phenylpropyl)-(S)-alanyl]-2-oxa-7-azaspiro[4.5]decane-6(S)-carboxylic acid;
7-[N-(1-carboethoxy-3-phenylpropyl)glycyl]-2-thia-7-azaspiro[4.4]nonane-8(S)-carboxylic acid;
7-[N-(1-carboxy-3-phenylpropyl)glycyl]-2-thia-7-azaspiro[4.4]nonane-8(S)-carboxylic acid;
2-[N-(1-carboethoxy-3-phenylpropyl)-(S)-alanyl]-7-oxa-2-azaspiro[4.5]decane-3(S)-carboxylic acid;
2-[N-(1-carboethoxy-3-phenylpropyl)-(S)-alanyl]-8-oxa-2-azaspiro[4.5]decane-3(S)-carboxylic acid;
1-[N-(1-carboxy-3-phenylpropyl)-(S)-alanyl]-7-oxa-1-azaspiro[4.5]decane-2(S)-carboxylic acid;
6-[N-(1-carboethoxy-3-phenylpropyl)-(S)-alanyl]-2-thia-6-azaspiro[4.5]decane-7(S)-carboxylic acid;
7-[N-(1-carboethoxy-3-phenylpropyl)-(S)-alanyl]-2-thia-7-azaspiro[4.5]decane-8(S)-carboxylic acid;
8-[N-(1-carboethoxy-3-phenylpropyl)-(S)-alanyl]-2-thia-8-azaspiro[4.5]decane-7(S)-carboxylic acid;
7-[N-(1-carboethoxy-3-phenylpropyl)-(S)-alanyl]-2-thia-7-azaspiro [4.5]decane-6(S)-carboxylic acid;
1-[N-(1-carboethoxy-3-phenylpropyl)-(S)-alanyl]-8-oxa-1-azaspiro[5.5]undecane-2(S)-carboxylic acid;
1-[N-(1-carboethoxy-3-phenylpropyl)-(S)-alanyl]-9-oxa-1-azaspiro[5.5]undecane-2(S)-carboxylic acid;
8-[N-(1-carboethoxy-3-phenylpropyl)-(S)-alanyl]-2-oxa-8-azaspiro[5.5]undecane-9(S)-carboxylic acid;
2-[N-(1-carboethoxy-3-phenylpropyl)-(S)-alanyl]-9-oxa-2-azaspiro[5.5]undecane-3(S)-carboxylic acid;
9-[N-(1-carboethoxy-3-phenylpropyl)-(S)-alanyl]-2-oxa-9-azaspiro[5.5]undecane-8(S)-carboxylic acid;
9-[N-(1-carboethoxy-3-phenylpropyl)-(S)-alanyl]-3-oxa-9-azaspiro[5.5]undecane-8(S)-carboxylic acid;
8-[N-(1-carboethoxy-3-phenylpropyl)-(S)-alanyl]-2-oxa-8-azaspiro[5.5 ]undecane-7(S)-carboxylic acid;
8-[N-(1-carboethoxy-3-phenylpropyl)-(S)-alanyl]-3-oxa-8-azaspiro[5.5]undecane-7(S)-carboxylic acid;
7-[N-(1-carbomethoxy-3-methylthio)-(R,S)-alanyl]-2-thia-7-azaspiro[4.4]nonane-8(S)-carboxylic acid;
N-(1-carboxy-2-benzyloxyethyl)-(S)-alanyl-(S)-proline;
N-(1-carboxy-2-benzylthioethyl)-(S)-alanyl-(S)-proline;
1-[N-(1-carboethoxy-2-benzyloxyethyl)-(S)-alanyl]octahydroindole-2(S)-carboxylic acid;
1-[N-(1-carboethoxy-2-benzylthioethyl)-(S)-alanyl]octahydroindole- 2(S)-carboxylic acid;
1-[N-(1-carboxy-2-benzyloxyethyl)-(S)-alanyl]octahydroindole-2(S)-carboxylic acid;
1-[N-(1-carboxy-2-benzylthioethyl)-(S)-alanyl]octahydroindole-2(S)-carboxylic acid;
7-[N-(1-carboethoxy-2-benzyloxyethyl)-(S)-alanyl]-1,4-dithia-7-azaspiro[4.4]nonane-8(S)-carboxylic acid;
7-[N-(1-carboethoxy-2-benzylthioethyl)-(S)-alanyl]-1,4-dithia-7-azaspiro[4.4]nonane-8(S)-carboxylic acid;
1-[N-(1-carboethoxy-2-benzyloxyethyl)-(S)-alanyl]-decahydrocyclohepta[b]pyrrole-2(S)-carboxylic acid;
1-[N-(1-carboethoxy-2-benzylthioethyl)-(S)-alanyl]-decahydrocyclohepta[b]pyrrole-2(S)-carboxylic acid;
N-[1-carboethoxy-2- (4-chlorobenzyloxy) ethyl]-(S)-alanyl-(S)-proline;
N-[1-carboethoxy-2- (4-chlorobenzylthio) ethyl]-(S)-alanyl-(S)-proline;
N-[1-carboethoxy-2- (4-chlorobenzyloxy) ethyl]-(S)-alanyl octahydroindole-2(S)-carboxylic acid;
1N-[1-carboethoxy-2-(4-chlorobenzylthio )ethyl]-(S)-alanyl octahydroindole-2(S)-carboxylic acid;
1-[N-(1-Carbomethoxy-3-phenylpropyl)-(S)-alanyl]-3a (S), 7a(S)-octahydroindole-2(S)-carboxylic acid;
7-[N-1(S)-Carboethoxy-3-phenylpropyl)-(S)-alanyl]-1,4-dithia-7-azaspiro[4.4]nonane-8(S)-carboxylic acid;
N-[1(S)-Carboethoxy-2-benzyloxyethyl]-(S)-alanyl-(S)-proline;
1-[N-(1(S)-Carboethoxy-2-benzyloxyethyl)-(S)-alanyl]-3a(S),7a(S)-octahydroindole-2-(S)-carboxylic acid;
1-[N-(1(R) -Carboethoxy-2-benzylthioethyl)-(S)-alanyl]-3a(S),7a(S)-octahydroindole-2(S)-carboxylic acid; and
N-[1(R) -Carboethoxy-2-benzylthioethyl]-(S)-alanyl-(S)-proline.

The compounds of this invention are useful in view of their pharmacological properties. In particular, they possess activity as antihypertensive agents as evidenced by their ability to reduce blood pressure in mammals, including humans, in which the blood pressure has become abnormally elevated.

The compounds of the present invention can be combined with pharmaceutical carriers and administered in a variety of well known pharmaceutical forms suitable for oral or parenteral administration to provide compositions useful in the treatment of cardiovascular disorders and particularly mammalian hypertension.

The effective dose (ED50) of the compounds of this invention will typically be in the range of about 0.01 to about 30 mg/kg, preferably about 0.1 to about 10 mg/kg, of mammalian weight, administered in single or divided doses. The exact dose to be administered is dependent upon where the particular compound lies within the above quoted range, as well as upon the age, weight and condition of the individual.

Generally, in treating humans, the compounds of this invention may be administered to patients in need of such treatment in a dosage range of 5 to 500 mg per patient generally given several times, thus giving a total daily dose of from 5 to 2000 mg per day. Also, the compounds of this invention may be given in combination with diuretics or other antihypertensives. Typically, these are combinations whose individual per day dosages range from one-fifth of the minimally recommended clinical dosages to the maximum recommended levels for the entities when they are given singly. Examples of such diuretics or other antihypertensives are hydrochlorothiazide, chlorothiazide, ethacrynic acid, amiloride, furosemide, propanolol, timolol and methyldopa.

The composition containing the compounds of this invention will preferably contain from about 5 to about 250 mg of the active compound per dosage unit. These compositions are most preferably administered orally. Typical formulations for oral administration are those such as tablets, capsules, syrups, elixirs or suspensions. Typical injectable formulations include solutions and suspensions.

Typical acceptable phamaceutical carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tri-calcium phosphate; sodium sulfate; calcium sulfate, polyvinylpyrrolidone, polyvinyl alcohol; stearic acid; alkaline earth metal stearates such as magnesium stearate and calcium stearate, stearic acid vegetable oils such as peanut oil, cottonseed oil, sesame oil, olive oil and corn oil; non-ionic, cationic and anionic surfactants;

ethylene gylcol polymers; beta-cyclodextrin; fatty alcohols and hydrolyzed cereal solids; as well as other nontoxic compatible fillers, binders, disintegrants, buffers, preservatives, antioxidants, lubricants, flavoring agents, and the like commonly used in pharmaceutical formulations.

The following examples describe in detail compositions that are illustrative of the present invention. It will be apparent to those skilled in the art that many modifications, both of materials and methods, may be practiced without departing from the purpose and intent of this disclosure.

In the following examples, the active ingredient is 1{[N-[1(S)-carboethoxy-3-phenylpropyl]-(S)-alanyl}-3a (S),7a (S)-octahydroindole-2(S)-carboxylic acid.

EXAMPLE 65

| Capsule | Amount (mg) | |
| --- | --- | --- |
| Active ingredient | 250.0 | 125.0 |
| Lactose | 173.0 | 86.5 |
| Corn Starch | 75.0 | 37.5 |
| Magnesium Stearate | 2.0 | 1.0 |
| | 500.0 | 250.0 |

Blend the active ingredient, lactose and corn starch until uniform; then blend the magnesium stearate into the resulting powder. Encapsulate the mixture into suitably sized two-piece hard gelatin capsules.

EXAMPLE 66

| Tablet | Amount (mg) | |
| --- | --- | --- |
| Active ingredient | 250.0 | 125.0 |
| Lactose | 161.0 | 80.5 |
| Corn Starch | 12.0 | 6.0 |
| Water (per thousand tablets) | 120 ml (evaporates) | 60 ml (evaporates) |
| Corn Starch | 75.0 | 37.5 |
| Magnesium Stearate | 2.0 | 1.0 |
| | 500.0 | 250.0 |

Blend the active ingredient with the lactose until uniform. Blend the smaller quantity of corn starch with the water and add the resulting corn starch paste, then mix until a uniform wet mass is formed. Add the remaining corn starch to the remaining wet mass and mix until uniform granules are obtained. Screen the granules through a suitable milling machine, using a ¾ inch stainless steel screen. Dry the milled granules in a suitable drying oven until the desired moisture content is obtained. Mill the dried granules through a suitable milling machine using a 16 mesh stainless steel screen. Blend in the magnesium stearate and compress the resulting mixture into tablets of desired shape, thickness, hardness and disintegration.

EXAMPLE 67

| Injectable Solution | mg/ml |
| --- | --- |
| Active ingredient | 5.00 |
| Methyl p-hydroxybenzoate | 0.80 |
| Propyl p-hydroxybenzoate | 0.10 |
| Disodium Edetate | 0.10 |
| Citric Acid Monohydrate | 0.08 |
| Dextrose | 40.0 |
| Water for injection qs. ad. | 1.0 ml |

Dissolve the p-hydroxybenzoates in a portion of water for injection at 60°–70° C. and cool the solution to 25°–35° C. Charge and dissolve all other excipients and the active ingredient. Bring the solution to final volume, filter it through a sterilizing membrane and fill into sterile containers.

Following the procedures of Examples 65, 66 and 67, substitute 1-[N-(1-carbomethoxy-3-phenylpropyl)-(S)-alanyl]octahydroindole-2(S)-carboxylic acid; 1-[N-(1-carboxy-3-phenylpropyl)-(S)-alanyl]octahydroindole-2(S)-carboxylic acid; N-[l(S)-carboethoxy-2-benzyloxyethyl]-(S)-alanyl-(S)-proline; or N-[1(R)-carboethoxy-2-benzylthioethyl]-(S)-alanyl-(S)-proline for 1-[N-[1(S)-carboethoxy-3-phenylpropyl]-(S)-alanyl-octahydroindole-2(S)-carboxylic acid to prepare other compositions of the present invention. Similarly, substitute other compounds of the present invention for 1-{[N-[1(S)-carboethoxy-3-phenylpropyl]-(S)-alanyl]octahydroindole-2(S)-carboxylic acid to prepare other compositions of the present invention.

We claim:

1. 1-[N-(1-carboethoxy-3-phenylpropyl)-(S)-alanyl]octahydrocyclopenta [b]pyrrole-2(S)-carboxylic acid.

2. The compound named 1-[N-(1-carboxy-3-phenylpropyl)-(S)-alanyl]octahydrocyclopenta [b]pyrrole-2(S)-carboxylic acid.

3. A method for reducing blood pressure in hypertensive mammals which comprises administering to such a mammal a composition comprising an effective amount of a compound of claim 1 together with a pharmaceutically acceptable carrier therefor.

4. A method for reducing blood pressure in hypertensive mammals which comprises administering to such a mammal a composition comprising an effective amount of a compound of claim 2 together with a pharmaceutically acceptable carrier therefor.

* * * * *